(12) United States Patent
Itagaki et al.

(10) Patent No.: US 7,288,674 B2
(45) Date of Patent: Oct. 30, 2007

(54) OPTICALLY ACTIVE BISOXAZOLINE COMPOUNDS, PROCESS FOR PRODUCTION OF THE SAME AND USE THEREOF

(75) Inventors: Makoto Itagaki, Katano (JP); Katsuhisa Masumoto, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/544,494

(22) PCT Filed: Feb. 4, 2004

(86) PCT No.: PCT/JP2004/001133

§ 371 (c)(1), (2), (4) Date: Aug. 4, 2005

(87) PCT Pub. No.: WO2004/069815

PCT Pub. Date: Aug. 19, 2004

(65) Prior Publication Data

US 2006/0149077 A1    Jul. 6, 2006

(30) Foreign Application Priority Data

Feb. 7, 2003 (JP) .............................. 2003-030547
May 16, 2003 (JP) .............................. 2003-138621

(51) Int. Cl.
C07C 61/04 (2006.01)
C07D 263/10 (2006.01)

(52) U.S. Cl. ...................................... 562/506; 548/239

(58) Field of Classification Search ................ 562/506; 548/237, 239
See application file for complete search history.

(56) References Cited

U.S. PATENT DOCUMENTS 6,072,081 A    6/2000 Itagaki et al.
6,858,559 B2   2/2005 Yamamoto et al.

FOREIGN PATENT DOCUMENTS

JP    62-114970 A    5/1987
JP    2-3628 A       1/1990
JP    11-171874 A    6/1999
JP    2003-12675 A   1/2003

OTHER PUBLICATIONS

Evans, D.A. et al., Journal of the American Chemical Society, 1999, vol. 121, No. 33, pp. 7559 to 7573.
Crosignani, S. et al., Tetrahedron, 1998, vol. 54, No. 51, pp. 15721 to 15730.
Nohira, Hiroyuki, Kagaku Zokan 97, Kagaku Dojin, 1982, pp. 165 to 174.
Lowenthal, R.E. et al., Tetrahedron Letters, 1990, vol. 31, No. 42, pp. 6005 to 6008.
Lowenthal, R.E. et al., Tetrahedron Letters, 1991, vol. 32, No. 50, pp. 7373 to 7376.
Dave, R.H., et al., Tetrahedron 55, 1999, pp. 11295-11308.

Primary Examiner—Rebecca Anderson
Assistant Examiner—Karen Cheng
(74) Attorney, Agent, or Firm—Birch, Stewart, Kolasch & Birch, LLP

(57) ABSTRACT

Optically active bisoxazoline compounds represented by the general formula (1), a process for producing the compounds, and a process for producing cyclopropanecarboxylic esters by using the same:

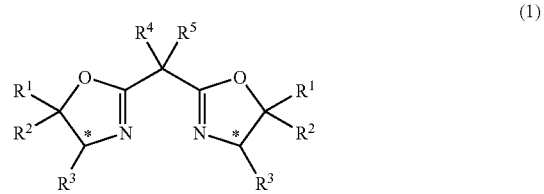

(1)

wherein $R^1$ and $R^2$ are the same and each represents $C_{1-6}$ alkyl, substituted or unsubstituted aralkyl, or substituted or unsubstituted phenyl or $R^1$ and $R^2$ are bonded each other together with the carbon atom of oxazoline ring to which they are bonded to form a ring; $R^3$ is substituted or unsubstituted naphthyl; $R^4$ and $R^5$ are the same and each represent hydrogen or $C_{1-6}$ alkyl, or $R^4$ and $R^5$ are bonded each other together with the carbon atom to which they are bonded to form a cycloalkyl ring having 3 to 6 carbon atoms; and * represents an asymmetric center.

1 Claim, No Drawings

OPTICALLY ACTIVE BISOXAZOLINE COMPOUNDS, PROCESS FOR PRODUCTION OF THE SAME AND USE THEREOF

The present application is a National Phase Application under 35 USC § 371 of PCT International Application No. PCT/JP2004/001133 filed on Feb. 4, 2004, and additionally claims priority under the provisions of 35 USC § 119 to JP 2003-030547 and JP 2003-138621, which were filed in the Japan Patent Office (JPO) on Feb. 7, 2003 and May 16, 2003, respectively.

TECHNICAL FIELD

The present invention relates to optically active bisoxazoline compounds, process for production of the same and use thereof.

BACKGROUND ART

Methods for producing optically active cyclopropane compounds, which are very important compounds as synthesis intermediates of agricultural chemicals such as synthesized pyrethroid type insecticides, pharmaceuticals, etc., and whose representative example is (+)-2,2-dimethyl-3-(2-methyl-1-propenyl)cyclopropanecarboxylic acid, from prochiral olefins have been known as an asymmetric reaction using an optically active bisoxazoline compound as a ligand (e.g. JP 11-171874 A, Tetrahedron Lett., 32, 7373 (1991)). These methods are relatively good in the diastereoselectivity (trans-isomer/cis-isomer ratio) and enantioselectivity. However, from an industrial viewpoint, it is desired to further improve the yield of the desired optically active cyclopropane compounds.

DISCLOSURE OF THE INVENTION

According to the present invention, an optically active bisoxazoline compound having naphthyl group as an asymmetric synthesis catalyst component can be easily obtained, and an optically active compound can be obtained at a high yield by using an industrially advantageous asymmetric catalyst comprising the optically active bisoxazoline compound and a copper compound.

That is, the present invention provides an optically active bisoxazoline compound represented by the formula (1):

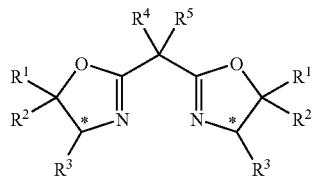

wherein $R^1$ and $R^2$ are the same, and each represents a $C_{1-6}$ alkyl group, a substituted or unsubstituted aralkyl group, or a substituted or unsubstituted phenyl group, or $R^1$ and $R^2$ are bonded each other together with the carbon atom of the oxazoline ring to which they are bonded to form a ring; $R^3$ represents a substituted or unsubstituted naphthyl group (preferably a 1-naphthyl group or a 2-naphthyl group); $R^4$ and $R^5$ are the same, and each represents a hydrogen atom or a $C_{1-6}$ alkyl group, or $R^4$ and $R^5$ are bonded each other together with the carbon atom to which they are bonded to form a cycloalkyl ring having 3 to 6 carbon atoms; and * represents an asymmetric center; a process for production of the same and use thereof.

BEST MODE FOR CARRYING OUT THE PRESENT INVENTION

First, the optically active bisoxazoline compound represented by the formula (1) (hereinafter, simply referred to as the optically active bisoxazoline compound (1)), which is a novel compound, will be illustrated.

Examples of the $C_{1-6}$ alkyl group represented by $R^1$ and $R^2$ include straight chain or branched alkyl groups such as a methyl, ethyl, n-propyl, isopropyl, n-butyl, isobutyl, n-pentyl, and n-hexyl group, and as the ring formed by bonding $R^1$ and $R^2$ each other together with the carbon atom of the oxazoline ring to which they are bonded, cycloalkyl rings having 3 to 7 carbon atoms can be exemplified. Examples of the cycloalkyl ring include a cyclopropane ring, a cyclobutane ring, a cyclopentane ring, a cyclohexane ring, and a cycloheptane ring.

Examples of the substituted or unsubstituted phenyl group represented by $R^1$ and $R^2$ include an unsubstituted phenyl group; a phenyl group substituted with a $C_{1-6}$ alkyl such as a 3-methylphenyl and 4-methylphenyl group; and a phenyl group substituted with a $C_{1-6}$ alkoxy group (e.g. a methoxy, ethoxy, propoxy, butoxy, pentyloxy, and hexyloxy group) such as a 2-methoxyphenyl, 3-methoxyphenyl, and 4-methoxyphenyl group.

As the substituted or unsubstituted aralkyl group, there is, for example, a $C_{1-6}$ alkyl group substituted with the above substituted or unsubstituted aryl group. Examples thereof include a benzyl, 2-methylbenzyl, 3-methylbenzyl, 4-methylbenzyl, 2-methoxybenzyl, 3-methoxybenzyl, 4-methoxybenzyl, 1-naphthylmethyl, and 2-naphthylmethyl group.

In the formula representing the optically active bisoxazoline compound (1), as the substituted or unsubstituted naphthyl group represented by $R^3$, in addition to an unsubstituted 1-naphthyl or 2-naphtyl group, there are, for example, a 1-naphthyl or 2-naphtyl group substituted with at least one $C_{1-6}$ alkyl or $C_{1-6}$ alkoxy group. Examples of the $C_{1-6}$ alkyl or $C_{1-6}$ alkoxy group include those exemplified with respect to the substituent $R^1$ or $R^2$. Specifically, there are, for example, a 4-fluoro-1-naphthyl, 2-methyl-1-naphthyl, 4-methyl-1-naphthyl, 2-methoxy-1-naphthyl, 2-ethoxy-1-naphthyl, 4-methoxy-1-naphthyl, 2,4-dimethoxy-1-naphthyl, 2-naphthyl, 7-methyl-2-naphthyl, 1-n-propyl-2-naphthyl, 6-methoxy-2-naphthyl, and 3,8-dimethoxy-2-naphthyl group. Among them, 1-naphthyl and 2-naphthyl group are preferable.

Examples of the $C_{1-6}$ alkyl group represented by $R^4$ and $R^5$ include a $C_{1-3}$ alkyl group such as a methyl, ethyl, n-propyl, and isopropyl group, and a butyl, pentyl, and hexyl group. As the ring formed by bonding $R^4$ and $R^5$ each other together with the carbon atom of the oxazoline ring to which they are bonded, cycloalkyl rings having 3 to 6 carbon atoms can be exemplified. Examples of the cycloalkyl ring include a cyclopropane ring, a cyclobutane ring, a cyclopentane ring, and a cyclohexane ring. Preferably, $R^4$ and $R^5$ represent a hydrogen atom, a $C_{1-3}$ alkyl group or a cycloalkyl ring having 3 to 6 carbon atoms formed by bonding $R^4$ and $R^5$ each other together with the carbon atom of the oxazoline ring to which they are bonded, and more preferably, they represent a $C_{1-3}$ alkyl group.

In the bisoxazoline compounds represented by the formula (1), there are two asymmetric carbon atoms represented by * and the compounds wherein both asymmetric carbon atoms are (S), or (R) configurations are preferably used.

Specific examples of such optically active bisoxazoline compounds (1) include bis[2-[(4S)-(1-naphthyl)-5,5-dimethyloxazoline]]methane, bis[2-[(4S)-(1-naphthyl)-5,5-diethyloxazoline]]methane, bis[2-[(4S)-(1-naphthyl)-5,5-di-n-propyloxazoline]]methane, bis[2-[(4S)-(1-naphthyl)-5,5-di-n-butyloxazoline]]methane, bis[2-[(4S)-(1-naphthyl)-5,5-diisobutyloxazoline]]methane, bis[2-[(4S)-(1-naphthyl)-5,5-di-n-pentyloxazoline]]methane, bis[2-[(4S)-(1-naphthyl)-5,5-di-n-hexyloxazoline]]methane, bis[2-[(4S)-(1-naphthyl)-5,5-dibenzyloxazoline]]methane, bis[2-[(4S)-(1-naphthyl)-5,5-di(2-methylbenzyl)oxazoline]]methane, bis[2-[(4S)-(1-naphthyl)-5,5-di(3-methylbenzyl)oxazoline]]methane, bis[2-[(4S)-(1-naphthyl)-5,5-di(4-methylbenzyl)oxazoline]]methane, bis[2-[(4S)-(1-naphthyl)-5,5-di(2-methoxybenzyl)oxazoline]]methane, bis[2-[(4S)-(1-naphthyl)-5,5-di(3-methoxybenzyl)oxazoline]]methane, bis[2-[(4S)-(1-naphthyl)-5,5-di(4-methoxybenzyl)oxazoline]]methane, bis[2-[(4S)-(1-naphthyl)-5,5-di(1-naphthylmethyl)oxazoline]]methane, bis[2-[(4S)-(1-naphthyl)-5,5-di(2-naphthylmethyl)oxazoline]]methane, bis[2-[(4S)-(1-naphthyl)-5,5-diphenyloxazoline]]methane, bis[2-[(4S)-(1-naphthyl)-5,5-di(3-methylphenyl)oxazoline]]methane, bis[2-[(4S)-(1-naphthyl)-5,5-di(4-methylphenyl)oxazoline]]methane, bis[2-[(4S)-(1-naphthyl)-5,5-di(2-methoxyphenyl)oxazoline]]methane, bis[2-[(4S)-(1-naphthyl)-5,5-di(3-methoxyphenyl)oxazoline]]methane, bis[2-[(4S)-(1-naphthyl)-5,5-di(4-methoxyphenyl)oxazoline]]methane, bis[2-[spiro[(4S)-(1-naphthyl)oxazoline-5,1'-cyclopropane]]]methane, bis[2-[spiro[(4S)-(1-naphthyl)oxazoline-5,1'-cyclobutane]]]methane, bis[2-[spiro[(4S)-(1-naphthyl)oxazoline-5,1'-cyclopentane]]]methane, bis[2-[spiro[(4S)-(1-naphthyl)oxazoline-5,1'-cyclohexane]]]methane, bis[2-[spiro[(4S)-methyloxazoline-5,1'-cycloheptane]]]methane, 2,2-bis[2-[(4S)-(1-naphthyl)-5,5-dimethyloxazoline]]propane, 2,2-bis[2-[(4S)-(1-naphthyl)-5,5-diethyloxazoline]]propane, 2,2-bis[2-[(4S)-(1-naphthyl)-5,5-di-n-propyloxazoline]]propane, 2,2-bis[2-[(4S)-(1-naphthyl)-5,5-di-n-butyloxazoline]]propane, 2,2-bis[2-[(4S)-(1-naphthyl)-5,5-diisobutyloxazoline]]propane, 2,2-bis[2-[(4S)-(1-naphthyl)-5,5-di-n-pentyloxazoline]]propane, 2,2-bis[2-[(4S)-(1-naphthyl)-5,5-di-n-hexyloxazoline]]propane, 2,2-[2-bis[2-(4S)-(1-naphthyl)-5,5-dibenzyloxazoline]]propane, 2,2-[2-bis[2-bis(4S)-(1-naphthyl)-5,5-di(2-methylbenzyl)oxazoline]]propane, 2,2-bis[2-[(4S)-(1-naphthyl)-5,5-di(3-methylbenzyl)oxazoline]]propane, 2,2-bis[2-[(4S)-(1-naphthyl)-5,5-di(4-methylbenzyl)oxazoline]]propane, 2,2-bis[2-[(4S)-(1-naphthyl)-5,5-di(2-methoxybenzyl)oxazoline]]propane, 2,2-bis[(4S)-(1-naphthyl)-5,5-di(3-methoxybenzyl)oxazoline]]propane, 2,2-bis[2-[(4S)-(1-naphthyl)-5,5-di(4-methoxybenzyl)oxazoline]]propane, 2,2-bis[2-[(4S)-(1-naphthyl)-5,5-di(1-naphthylmethyl)oxazoline]]propane, 2,2-bis[(4S)-(1-naphthyl)-5,5-di(2-naphthylmethyl)oxazoline]]propane, 2,2-bis[(4S)-(1-naphthyl)-5,5-diphenyloxazoline]]propane, 2,2-bis[2-[(4S)-(1-naphthyl)-5,5-di(3-methylphenyl)oxazoline]]propane, 2,2-bis[2-[(4S)-(1-naphthyl)-5,5-di(4-methylphenyl)oxazoline]]propane, 2,2-bis[2-[(4S)-(1-naphthyl)-5,5-di(2-methoxyphenyl)oxazoline]]propane, 2,2-bis[2-[(4S)-(1-naphthyl)-5,5-di(3-methoxyphenyl)oxazoline]]propane, 2,2-bis[2-[(4S)-(1-naphthyl)-5,5-di(4-methoxyphenyl)oxazoline]]propane, 2,2-bis[2-[spiro[(4S)-(1-naphthyl)oxazoline-5,1'-cyclopropane]]]propane, 2,2-bis[2-[spiro[(4S)-(1-naphthyl)oxazoline-5,1'-cyclobutane]]]propane, 2,2-bis[2-[spiro[(4S)-(1-naphthyl)oxazoline-5,1'-cyclopentane]]]propane, 2,2-bis[2-[spiro[(4S)-(1-naphthyl)oxazoline-5,1'-cyclohexane]]]propane, 2,2-bis[2-[spiro[(4S)-methyloxazoline-5,1'-cycloheptane]]]propane, 3,3-bis[2-[(4S)-(1-naphthyl)-5,5-dimethyloxazoline]]pentane, 3,3-bis[2-[(4S)-(1-naphthyl)-5,5-diethyloxazoline]]pentane, 3,3-bis[2-[(4S)-(1-naphthyl)-5,5-di-n-propyl-2-oxazoline]]pentane, 3,3-bis[2-[(4S)-(1-naphthyl)-5,5-di-n-butyloxazoline]]pentane, 3,3-bis[2-[(4S)-(1-naphthyl)-5,5-diisobutyloxazoline])pentane, 3,3-bis[2-[(4S)-(1-naphthyl)-5,5-di-n-pentyloxazoline]]pentane, 3,3-bis[2-[(4S)-(1-naphthyl)-5,5-di-n-hexyloxazoline]]pentane, 3,3-bis[2-[(4S)-(1-naphthyl)-5,5-dibenzyloxazoline]]pentane, 3,3-bis[2-bis[(4S)-(1-naphthyl)-5,5-di(2-methylbenzyl)oxazoline]]pentane, 3,3-bis[2-[(4S)-(1-naphthyl)-5,5-di(3-methylbenzyl)oxazoline]]pentane, 3,3-bis[2-[(4S)-(1-naphthyl)-5,5-di(4-methylbenzyl)oxazoline]]pentane, 3,3-bis[2-[(4S)-(1-naphthyl)-5,5-di(2-methoxybenzyl)oxazoline]]pentane, 3,3-bis[(4S)-(1-naphthyl)-5,5-di(3-methoxybenzyl)oxazoline]]pentane, 3,3-bis[2-[(4S)-(1-naphthyl)-5,5-di(4-methoxybenzyl)oxazoline]]pentane, 3,3-bis[2-[(4S)-(1-naphthyl)-5,5-di(1-naphthylmethyl)oxazoline]]pentane, 3,3-[2-bis[(4S)-(1-naphthyl)-5,5-di(2-naphthylmethyl)oxazoline]]pentane, 3,3-[2-bis[(4S)-(1-naphthyl)-5,5-diphenyloxazoline]]pentane, 3,3-bis[2-[(4S)-(1-naphthyl)-5,5-di(3-methylphenyl)oxazoline]]pentane, 3,3-bis[2-[(4S)-(1-naphthyl)-5,5-di(4-methylphenyl)oxazoline]]pentane, 3,3-bis[2-[(4S)-(1-naphthyl)-5,5-di(2-methoxyphenyl)oxazoline]]pentane, 3,3-bis[2-[(4S)-(1-naphthyl)-5,5-di(3-methoxyphenyl)oxazoline]]pentane, 3,3-bis[2-[(4S)-(1-naphthyl)-5,5-di(4-methoxyphenyl)oxazoline]]pentane, 3,3-bis[2-[spiro[(4S)-(1-naphthyl)oxazoline-5,1'-cyclopropane]]]pentane, 3,3-bis[2-[spiro[(4S)-(1-naphthyl)oxazoline-5,1'-cyclobutane]]]pentane, 3,3-bis[2-[spiro[(4S)-(1-naphthyl)oxazoline-5,1'-cyclopentane]]]pentane, 3,3-bis[2-[spiro[(4S)-(1-naphthyl)oxazoline-5,1'-cyclohexane]]]pentane, 3,3-bis[2-[spiro[(4S)-methyloxazoline-5,1'-cycloheptane]]]pentane, 4,4-bis[2-[(4S)-(1-naphthyl)-5,5-dimethyloxazoline]]heptane, 4,4-bis[2-[(4S)-(1-naphthyl)-5,5-diethyl-2-oxazoline]]heptane, 4,4-bis[2-[(4S)-(1-naphthyl)-5,5-di-n-propyloxazoline]]heptane, 4,4-bis[2-[(4S)-(1-naphthyl)-5,5-di-n-butyloxazoline]]heptane, 4,4-bis[2-[(4S)-(1-naphthyl)-5,5-diisobutyloxazoline]]heptane, 4,4-bis[2-[(4S)-(1-naphthyl)-5,5-di-n-pentyloxazoline]]heptane, 4,4-[2-bis[2-[(4S)-(1-naphthyl)-5,5-di-n-hexyloxazoline]]heptane, 4,4-bis[2-[(4S)-(1-naphthyl)-5,5-dibenzyloxazoline]]heptane, 4,4-bis[2-bis[(4S)-(1-naphthyl)-5,5-di(2-methylbenzyl)oxazoline]]heptane, 4,4-bis[2-[(4S)-(1-naphthyl)-5,5-di(3-methylbenzyl)oxazoline]]heptane, 4,4-[2-[(4S)-(1-naphthyl)-5,5-di(4-methylbenzyl)oxazoline]]heptane, 4,4-bis[2-[(4S)-(1-naphthyl)-5,5-di(2-methoxybenzyl)oxazoline]]heptane, 4,4-[2-bis[(4S)-(1-naphthyl)-5,5-di(3-methoxybenzyl)oxazoline]]heptane, 4,4-bis[2-[(4S)-(1-naphthyl)-5,5-di(4-methoxybenzyl)oxazoline]]heptane, 4,4-bis[2-[(4S)-(1-naphthyl)-5,5-di(1-naphthylmethyl)oxazoline]]heptane, 4,4-[2-bis[(4S)-(1-naphthyl)-5,5-di(2-naphthylmethyl)oxazoline]]heptane, 4,4-bis[(4S)-(1-naphthyl)-5,5-diphenyloxazoline]]heptane, 4,4-bis[2-[(4S)-(1-naphthyl)-5,5-di(3-methylphenyl)oxazoline]]heptane, 4,4-bis[2-[(4S)-(1-naphthyl)-5,5-di(4-methylphenyl)oxazoline]]heptane, 4,4-bis[2-[(4S)-(1-naphthyl)-5,5-di(2-methoxyphenyl)oxazoline]]heptane, 4,4-bis[2-[(4S)-(1-naphthyl)-5,5-di(3-methoxyphenyl)oxazoline]]heptane, 4,4-bis[2-[(4S)-(1-naphthyl)-5,5-di(4-methoxyphenyl)oxazoline]]heptane, 4,4-bis[2-[spiro[(4S)-(1-naphthyl)oxazoline-5,1'-cyclopropane]]]heptane, 4,4-bis[2-[spiro

[(4S)-(1-naphthyl)oxazoline-5,1'-cyclobutane]]heptane, 4,4-bis[2-[spiro[(4S)-(1-naphthyl)oxazoline-5,1'-cyclopentane]]]heptane, 4,4-bis[2-[spiro[(4S)-(1-naphthyl)oxazoline-5,1'-cyclohexane]]]heptane, 4,4-bis[2-[spiro[(4S)-methyloxazoline-5,1'-cycloheptane]]]heptane, 1,1-bis[2-[(4S)-(1-naphthyl)-5,5-dimethyloxazoline]]cyclopropane, 1,1-bis[2-[(4S)-(1-naphthyl)-5,5-diethyloxazoline]]cyclopropane, 1,1-bis[2-[(4S)-(1-naphthyl)-5,5-di-n-propyl-2-oxazoline]]cyclopropane, 1,1-bis[2-[(4S)-(1-naphthyl)-5,5-di-n-butyloxazoline]]cyclopropane, 1,1-bis[2-[(4S)-(1-naphthyl)-5,5-diisobutyloxazoline]]cyclopropane, 1,1-bis[2-[(4S)-(1-naphthyl)-5,5-di-n-pentyloxazoline])cyclopropane, 1,1-bis[2-[(4S)-(1-naphthyl)-5,5-di-n-hexyloxazoline]]cyclopropane, 1,1-bis[2-[(4S)-(1-naphthyl)-5,5-dibenzyloxazoline]]cyclopropane, 1,1-bis[2-[(4S)-(1-naphthyl)-5,5-di(2-methylbenzyl)oxazoline]]cyclopropane, 1,1-bis[2-[(4S)-(1-naphthyl)-5,5-di(3-methylbenzyl)oxazoline]]cyclopropane, 1,1-bis[2-[(4S)-(1-naphthyl)-5,5-di(4-methylbenzyl)oxazoline]]cyclopropane, 1,1-bis[2-[(4S)-(1-naphthyl)-5,5-di(2-methoxybenzyl)oxazoline]]cyclopropane, 1,1-bis[(4S)-(1-naphthyl)-5,5-di(3-methoxybenzyl)oxazoline]]cyclopropane, 1,1-bis[2-[(4S)-(1-naphthyl)-5,5-di(4-methoxybenzyl)oxazoline]]cyclopropane, 1,1-bis[2-[(4S)-(1-naphthyl)-5,5-di(1-naphthylmethyl)oxazoline]]cyclopropane, 1,1-bis[2-[(4S)-(1-naphthyl)-5,5-di(2-naphthylmethyl)oxazoline]]cyclopropane, 1,1-bis[2-[(4S)-(1-naphthyl)-5,5-diphenyloxazoline]]cyclopropane, 1,1-bis[2-[(4S)-(1-naphthyl)-5,5-di(3-methylphenyl)oxazoline]]cyclopropane, 1,1-bis[2-[(4S)-(1-naphthyl)-5,5-di(4-methylphenyl)oxazoline]]cyclopropane, 1,1-bis[2-[(4S)-(1-naphthyl)-5,5-di(2-methoxyphenyl)oxazoline]]cyclopropane, 1,1-bis[2-[(4S)-(1-naphthyl)-5,5-di(3-methoxyphenyl)oxazoline]]cyclopropane, 1,1-bis[2-[(4S)-(1-naphthyl)-5,5-di(4-methoxyphenyl)oxazoline]]cyclopropane, 1,1-bis[2-[spiro[(4S)-(1-naphthyl)oxazoline-5,1'-cyclopropane]]]cyclopropane, 1,1-bis[2-[spiro[(4S)-(1-naphthyl)oxazoline-5,1'-cyclopentane]]]cyclopropane, 1,1-bis[2-[spiro[(4S)-methyloxazoline-5,1'-cycloheptane]]]cyclopropane, 1,1-bis[2-[(4S)-(1-naphthyl)-5,5-dimethyloxazoline]]cyclobutane, 1,1-bis[2-[(4S)-(1-naphthyl)-5,5-diethyloxazoline]]cyclobutane, 1,1-bis[2-[(4S)-(1-naphthyl)-5,5-di-n-propyl-2-oxazoline]]cyclobutane, 1,1-bis[2-[(4S)-(1-naphthyl)-5,5-di-n-butyloxazoline]]cyclobutane, 1,1-bis[2-[(4S)-(1-naphthyl)-5,5-diisobutyloxazoline]]cyclobutane, 1,1-bis[2-[(4S)-(1-naphthyl)-5,5-di-n-pentyloxazoline]]cyclobutane, 1,1-bis[2-[(4S)-(1-naphthyl)-5,5-di-n-hexyloxazoline]]cyclobutane, 1,1-bis[2-[(4S)-(1-naphthyl)-5,5-dibenzyloxazoline]]cyclobutane, 1,1-bis[2-[(4S)-(1-naphthyl)-5,5-di(2-methylbenzyl)oxazoline]]cyclobutane, 1,1-bis[2-[(4S)-(1-naphthyl)-5,5-di(3-methylbenzyl)oxazoline]]cyclobutane, 1,1-bis[2-[(4S)-(1-naphthyl)-5,5-di(4-methylbenzyl)oxazoline]]cyclobutane, 1,1-bis[2-[(4S)-(1-naphthyl)-5,5-di(2-methoxybenzyl)oxazoline]]cyclobutane, 1,1-bis[(4S)-(1-naphthyl)-5,5-di(3-methoxybenzyl)oxazoline]]cyclobutane, 1,1-bis[2-[(4S)-(1-naphthyl)-5,5-di(4-methoxybenzyl)oxazoline]]cyclobutane, 1,1-bis[2-[(4S)-(1-naphthyl)-5,5-di(1-naphthylmethyl)oxazoline]]cyclobutane, 1,1-bis[2-[(4S)-(1-naphthyl)-5,5-di(2-naphthylmethyl)oxazoline]]cyclobutane, 1,1-bis[2-[(4S)-(1-naphthyl)-5,5-diphenyloxazoline]]cyclobutane, 1,1-bis[2-[(4S)-(1-naphthyl)-5,5-di(3-methylphenyl)oxazoline]]cyclobutane, 1,1-bis[2-[(4S)-(1-naphthyl)-5,5-di(4-methylphenyl)oxazoline]]cyclobutane, 1,1-bis[2-[(4S)-(1-naphthyl)-5,5-di(2-methoxyphenyl)oxazoline]]cyclobutane, 1,1-bis[2-[(4S)-(1-naphthyl)-5,5-di(3-methoxyphenyl)oxazoline]]cyclobutane, 1,1-bis[2-[(4S)-(1-naphthyl)-5,5-di(4-methoxyphenyl)oxazoline]]cyclobutane, 1,1-bis[2-[spiro[(4S)-(1-naphthyl)oxazoline-5,1'-cyclopropane]]]cyclobutane, 1,1-bis[2-[spiro[(4S)-(1-naphthyl)oxazoline-5,1'-cyclobutane]]]cyclobutane, 1,1-bis[2-[spiro[(4S)-(1-naphthyl)oxazoline-5,1'-cyclopentane]]]cyclobutane, 1,1-bis[2-[spiro[(4S)-(1-naphthyl)oxazoline-5,1'-cyclohexane]]]cyclobutane, 1,1-bis[2-[spiro[(4S)-methyloxazoline-5,1'-cycloheptane]]]cyclobutane, 1,1-bis[2-[(4S)-(1-naphthyl)-5,5-dimethyloxazoline]]cyclopentane, 1,1-bis[2-[(4S)-(1-naphthyl)-5,5-diethyloxazoline]]cyclopentane, 1,1-bis(2-[(4S)-(1-naphthyl)-5,5-di-n-propyloxazoline]]cyclopentane, 1,1-bis[2-[(4S)-(1-naphthyl)-5,5-di-n-butyloxazoline]]cyclopentane, 1,1-bis[2-[(4S)-(1-naphthyl)-5,5-diisobutyloxazoline]]cyclopentane, 1,1-bis[2-[(4S)-(1-naphthyl)-5,5-di-n-pentyloxazoline]]cyclopentane, 1,1-bis[2-[(4S)-(1-naphthyl)-5,5-di-n-hexyloxazoline]]cyclopentane, 1,1-bis[2-[(4S)-(1-naphthyl)-5,5-dibenzyloxazoline]]cyclopentane, 1,1-bis[2-bis[(4S)-(1-naphthyl)-5,5-di(2-methylbenzyl)oxazoline]]cyclopentane, 1,1-bis[2-[(4S)-(1-naphthyl)-5,5-di(3-methylbenzyl)oxazoline]]cyclopentane, 1,1-bis[2-[(4S)-(1-naphthyl)-5,5-di(4-methylbenzyl)oxazoline]]cyclopentane, 1,1-bis[2-[(4S)-(1-naphthyl)-5,5-di(2-methoxybenzyl)oxazoline]]cyclopentane, 1,1-bis[2-[(4S)-(1-naphthyl)-5,5-di(3-methoxybenzyl)oxazoline]]cyclopentane, 1,1-bis[2-[(4S)-(1-naphthyl)-5,5-di (4-methoxybenzyl)oxazoline]]cyclopentane, 1,1-bis[2-[(4S)-(1-naphthyl)-5,5-di(1-naphthylmethyl)oxazoline]]cyclopentane, 1,1-bis[(4S)-(1-naphthyl)-5,5-di(2-naphthylmethyl)oxazoline]]cyclopentane, 1,1-bis[(4S)-(1-naphthyl)-5,5-diphenyloxazoline]]cyclopentane, 1,1-bis[2-[(4S)-(1-naphthyl)-5,5-di(3-methylphenyl)oxazoline]]cyclopentane, 1,1-bis[2-[(4S)-(1-naphthyl)-5,5-di(4-methylphenyl)oxazoline]]pentane, 1,1-bis[2-[(4S)-(1-naphthyl)-5,5-di(2-methoxyphenyl)oxazoline]]cyclopentane, 1,1-bis[2-[(4S)-(1-naphthyl)-5,5-di(3-methoxyphenyl)oxazoline]]cyclopentane, 1,1-bis[2-[(4S)-(1-naphthyl)-5,5-di (4-methoxyphenyl)oxazoline]]cyclopentane, 1,1-bis[2-[spiro[(4S)-(1-naphthyl)oxazoline-5,1'-cyclopropane]]]cyclopentane, 1,1-bis[2-[spiro[(4S)-(1-naphthyl)oxazoline-5,1'-cyclobutane]]]cyclopentane, 1,1-bis[2-[spiro[(4S)-(1-naphthyl)oxazoline-5,1'-cyclopentane]]]cyclopentane, 1,1-bis[2-[spiro[(4S)-(1-naphthyl)oxazoline-5,1'-cyclohexane]]]cyclopentane, 1,1-bis[2-[spiro[(4S)-methyloxazoline-5,1'-cycloheptane]]]cyclopentane, 1,1-bis[2-[(4S)-(1-naphthyl)-5,5-dimethyloxazoline]]cyclohexane, 1,1-bis[2-[(4S)-(1-naphthyl)-5,5-diethyloxazoline]]cyclohexane, 1,1-bis[2-[(4S)-(1-naphthyl)-5,5-di-n-propyloxazoline]]cyclohexane, 1,1-bis[2-[(4S)-(1-naphthyl)-5,5-di-n-butyloxazoline]]cyclohexane, 1,1-bis[2-[(4S)-(1-naphthyl)-5,5-diisobutyloxazoline]]cyclohexane, 1,1-bis[2-[(4S)-(1-naphthyl)-5,5-di-n-pentyloxazoline]]cyclohexane, 1,1-bis[2-[(4S)-(1-naphthyl)-5,5-di-n-hexyloxazoline]]cyclohexane, 1,1-bis[2-[(4S)-(1-naphthyl)-5,5-dibenzyloxazoline]]cyclohexane, 1,1-bis[2-bis[(4S)-(1-naphthyl)-5,5-di(2-methylbenzyl)oxazoline]]cyclohexane, 1,1-bis[2-[(4S)-(1-naphthyl)-5,5-di(3-methylbenzyl)oxazoline]]cyclohexane, 1,1-bis[2-[(4S)-(1-naphthyl)-5,5-di (4-methylbenzyl)oxazoline]]cyclohexane, 1,1-bis[2-[(4S)-(1-naphthyl)-5,5-di(2-methoxybenzyl)oxazoline]]cyclohexane, 1,1-bis[2-[(4S)-(1-naphthyl)-5,5-di(3-methoxybenzyl)oxazoline)]cyclohexane, 1,1-bis[2-[(4S)-(1-naphthyl)-5,5-di(4-methoxybenzyl)oxazoline]]cyclohexane, 1,1-bis[2-[(4S)-(1-naphthyl)-5,5-di(1-naphthylmethyl)oxazoline]]cyclohexane, 1,1-bis[(4S)-(1-naphthyl)-5,5-di(2- naphthylmethyl)oxazoline]]cyclohexane, 1,1-bis[[(4S)-(1-naphthyl)-5,5-diphenyloxazoline]]cyclohexane, 1,1-bis[2-[(4S)-(1-naphthyl)-5,5-di(3-methylphenyl)oxazoline]]cyclohexane, 1,1-bis[2-[(4S)-(1-naphthyl)-5,5-di(4-methylphenyl)oxazoline]]hexane, 1,1-bis[2-[(4S)-(1-naphthyl)-5,5-di(2-methoxyphenyl)oxazoline]]cyclohexane, 1,1-bis[2-[(4S)-(1-naphthyl)-5,5-di(3-methoxyphenyl)oxazoline]]cyclohexane, 1,1-bis[2-[(4S)-(1-naphthyl)-5,5-di(4-methoxyphenyl)oxazoline]]cyclohexane, 1,1-bis[2-[spiro[(4S)-(1-naphthyl)oxazoline-5,1'-cyclopropane]]]cyclohexane, 1,1-bis[2-[spiro[(4S)-(1-naphthyl)oxazoline-5,1'-cyclobutane]]]cyclohexane, 1,1-bis[2-[spiro[(4S)-(1-naphthyl)oxazoline-5,1'-cyclopentane]]]cyclohexane, 1,1-bis[2-[spiro[(4S)-(1-naphthyl)oxazoline-5,1'-cyclohexane]]]cyclohexane, 1,1-bis[2-[spiro[(4S)-methyloxazoline-5,1'-cycloheptane]]]cyclohexane; and these compounds in which 1-naphthyl group at the fourth place is replaced with 2-naphthyl group such as bis[2-[(4S)-(2-naphthyl)-5,5-dimethyloxazoline]]methane; these compounds of which the configuration (4S) at the fourth place is changed to (4R) such as bis[2-[(4R)-(1-naphthyl)-5,5-dimethyloxazoline]]methane and bis[2-[(4R)-(2-naphthyl)-5,5-dimethyloxazoline]]methane.

The optically active bisoxazoline compounds (1) can be produced by reacting an optically active diamide compound represented by the formula (2):

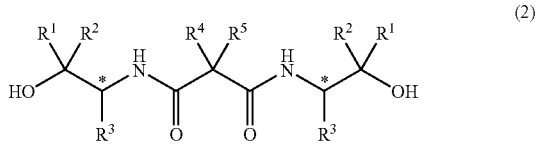

wherein $R^1$, $R^2$, $R^3$, $R^4$, $R^5$, and * are as defined above, which is a novel compound, (hereinafter, simply referred to as the optically active diamide compound (2)) with a Lewis acid.

Examples of the optically active diamide compounds (2) include N,N'-bis[(1S)-(1-naphthyl)-2-hydroxy-2-methylpropyl]propane-1,3-diamide, N,N'-bis[(1S)-(1-naphthyl)-2-hydroxy-2-ethylbutyl]propane-1,3-diamide, N,N'-bis[(1S)-(1-naphthyl)-2-hydroxy-2-n-propylpentyl]propane-1,3-diamide, N,N'-bis[(1S)-(1-naphthyl)-2-hydroxy-2-n-butylhexyl]propane-1,3-diamide, N,N'-bis[(1S)-(1-naphthyl)-2-hydroxy-2-isobutyl-4-methylpentyl]propane-1,3-diamide, N,N'-bis[(1S)-(1-naphthyl)-2-hydroxy-2-n-pentylheptyl]propane-1,3-diamide, N,N'-bis[(1S)-(1-naphthyl)-2-hydroxy-2-n-hexyloctyl]propane-1,3-diamide, N,N'-bis[(1S)-(1-naphthyl)-2-hydroxy-2-benzyl-3-phenylpropyl]propane-1,3-diamide, N,N'-bis[(1S)-(1-naphthyl)-2-hydroxy-2-(2-methylbenzyl)-3-(2-methylphenyl)propyl]propane-1,3-diamide, N,N'-bis[(1S)-(1-naphthyl)-2-hydroxy-2-(3-methylbenzyl)-3-(3-methylphenyl)propyl]propane-1,3-diamide, N,N'-bis[(1S)-(1-naphthyl)-2-hydroxy-2-(4-methylbenzyl)-3-(4-methylphenyl)propyl]propane-1,3-diamide, N,N'-bis[(1S)-(1-naphthyl)-2-hydroxy-2-(2-methoxybenzyl)-3-(2-methoxyphenyl)propyl]propane-1,3-diamide, N,N'-bis[(1S)-(1-naphthyl)-2-hydroxy-2-(3-methoxybenzyl)-3-(3-methoxyphenyl)propyl]propane-1,3-diamide, N,N'-bis[(1S)-(1-naphthyl)-2-hydroxy-2-(4-methoxybenzyl)-3-(4-methoxyphenyl)propyl]propane-1,3-diamide, N,N'-bis[(1S)-(1-naphthyl)-2-hydroxy-2-(1-naphthylmethyl)-3-(1-naphthyl)propyl]propane-1,3-diamide, N,N'-bis[(1S)-(1-naphthyl)-2-hydroxy-2-(2-naphthylmethyl)-3-(2-naphthyl)propyl]propane-1,3-diamide, N,N'-bis[(1S)-(1-naphthyl)-2-hydroxy-2,2-diphenylethyl]propane-1,3-diamide, N,N'-bis[(1S)-(1-naphthyl)-2-hydroxy-2,2-di(3-methyphenyl)ethyl]propane-1,3-diamide, N,N'-bis[(1S)-(1-naphthyl)-2-hydroxy-2,2-di(4-methylphenyl)ethyl]propane-1,3-diamide, N,N'-bis[(1S)-(1-naphthyl)-2-hydroxy-2,2-di(2-methoxyphenyl)ethyl]propane-1,3-diamide, N,N'-bis[(1S)-(1-naphthyl)-2-hydroxy-2,2-di(3-methoxyphenyl)ethyl]propane-1,3-diamide, N,N'-bis[(1S)-(1-naphthyl)(1-hydroxycyclopropyl)methyl]propane-1,3-diamide, N,N'-bis[(1S)-(1-naphthyl)(1-hydroxycyclobutyl)methyl]propane-1,3-diamide, N,N'-bis[(1S)-(1-naphthyl)(1-hydroxycyclopentyl)methyl]propane-1,3-diamide, N,N'-bis[(1S)-(1-naphthyl)(1-hydroxycyclohexyl)methyl]propane-1,3-diamide, N,N'-bis[(1S)-(1-naphthyl)(1-hydroxycycloheptyl)methyl]propane-1,3-diamide, N,N'-bis[(1S)-(1-naphthyl)-2-hydroxy-2-methylpropyl]-2,2-dimethylpropane-1,3-diamide, N,N'-bis[(1S)-(1-naphthyl)-2-hydroxy-2-ethylbutyl]-2,2-dimethylpropane-1,3-diamide, N,N'-bis[(1S)-(1-naphthyl)-2-hydroxy-2-n-propylpentyl]-2,2-dimethylpropane-1,3-diamide, N,N'-bis[(1S)-(1-naphthyl)-2-hydroxy-2-n-butylhexyl]-2,2-dimethylpropane-1,3-diamide, N,N'-bis[(1S)-(1-naphthyl)-2-hydroxy-2-isobutyl-4-methylpentyl]-2,2-dimethylpropane-1,3-diamide, N,N'-bis[(1S)-(1-naphthyl)-2-hydroxy-2-n-pentylheptyl]-2,2-dimethylpropane-1,3-diamide, N,N'-bis[(1S)-(1-naphthyl)-2-hydroxy-2-n-hexyloctyl]-2,2-dimethylpropane-1,3-diamide, N,N'-bis[(1S)-(1-naphthyl)-2-hydroxy-2-benzyl-3-phenylpropyl]-2,2-dimethylpropane-1,3-diamide, N,N'-bis[(1S)-(1-naphthyl)-2-hydroxy-2-(2-methylbenzyl)-3-(2-methylphenyl)propyl]-2,2-dimethylpropane-1,3-diamide, N,N'-bis[(1S)-(1-naphthyl)-2-hydroxy-2-(3-methylbenzyl)-3-(3-methylphenyl)propyl]-2,2-dimethylpropane-1,3-diamide, N,N'-bis[(1S)-(1-naphthyl)-2-hydroxy-2-(4-methylbenzyl)-3-(4-methylphenyl)propyl]-2,2-dimethylpropane-1,3-diamide, N,N'-bis[(1S)-(1-naphthyl)-2-hydroxy-2-(2-methoxybenzyl)-3-(2-methoxyphenyl)propyl]-2,2-dimethylpropane-1,3-diamide, N,N'-bis[(1S)-(1-naphthyl)-2-hydroxy-2-(3-methoxybenzyl)-3-(3-methoxyphenyl)propyl]-2,2-dimethylpropane-1,3-diamide, N,N'-bis[(1S)-(1-naphthyl)-2-hydroxy-2-(4-methoxybenzyl)-3-(4-methoxyphenyl)propyl]-2,2-dimethylpropane-1,3-diamide, N,N'-bis[(1S)-(1-naphthyl)-2-hydroxy-2-(1-naphthylmethyl)-3-(1-naphthyl)propyl]-2,2-dimethylpropane-1,3-diamide, N,N'-bis[(1S)-(1-naphthyl)-2-hydroxy-2-(2-naphthylmethyl)-3-(2-naphthyl)propyl]-2,2-dimethylpropane-1,3-diamide, N,N'-bis[(1S)-(1-naphthyl)-2-hydroxy-2,2-diphenylethyl]-2,2-dimethylpropane-1,3-diamide, N,N'-bis[(1S)-(1-naphthyl)-2-hydroxy-2,2-di(3-methylphenyl)ethyl]-2,2-dimethylpropane-1,3-diamide, N,N'-bis[(1S)-(1-naphthyl)-2-hydroxy-2,2-di(4-methylphenyl)ethyl]-2,2-dimethylpropane-1,3-diamide, N,N'-bis[(1S)-(1-naphthyl)-2-hydroxy-2,2-di(2-methoxyphenyl)ethyl]-2,2-dimethylpropane-1,3-diamide, N,N'-bis[(1S)-(1-naphthyl)-2-hydroxy-2,2-di(3-methoxyphenyl)ethyl]-2,2-dimethylpropane-1,3-diamide, N,N'-bis[(1S)-(1-naphthyl)(1-hydroxycyclopropyl)methyl]-2,2-dimethylpropane-1,3-diamide, N,N'-bis[(1S)-(1-naphthyl)(1-hydroxycyclobutyl)methyl]-2,2-dimethylpropane-1,3-diamide, N,N'-bis[(1S)-(1-naphthyl)(1-hydroxycyclopentyl)methyl]-2,2-dimethylpropane-1,3-diamide, N,N'-bis[(1S)-(1-naphthyl)(1-hydroxycyclohexyl)methyl]-2,2-dimethylpropane-1,3-diamide, N,N'-bis[(1S)-(1-naphthyl)(1-hydroxycycloheptyl)methyl]-2,2-dimethylpropane-1,3-diamide, N,N'-bis[(1S)-(1-naphthyl)-2-hydroxy-2-methylpropyl]-2,2-diethylpropane-1,3-diamide, N,N'-bis[(1S)-(1-naphthyl)-2-hydroxy-2-ethylbutyl]-2,2-diethylpropane-1,3-diamide, N,N'-bis[(1S)-(1-naphthyl)-2-hydroxy-2-n-propylpentyl]-2,2-diethylpropane-1,3-diamide, N,N'-bis[(1S)-(1-naphthyl)-2-hydroxy-2-n-butylhexyl]-2,2-diethylpropane-1,3-diamide, N,N'-bis[(1S)-(1-naphthyl)-2-hydroxy-2-isobutyl-4-methylpentyl]-2,2-diethylpropane-1,3-diamide, N,N'-bis[(1S)-(1-naphthyl)-2-hydroxy-2-n-pentylheptyl]-2,2-diethylpropane-1,3-diamide, N,N'-bis[(1S)-(1-naphthyl)-2-hydroxy-2-n-hexyloctyl]-2,2-diethylpropane-1,3-diamide, N,N'-bis[(1S)-(1-naphthyl)-2-hydroxy-2-benzyl-3-phenylpropyl]-2,2-diethylpropane-1,3-diamide, N,N'-bis[(1S)-(1-naphthyl)-2-hydroxy-2-(2-methylbenzyl)-3-(2-methylphenyl)propyl]-2,2-diethylpropane-1,3-diamide, N,N'-bis[(1S)-(1-naphthyl)-2-hydroxy-2-(3-methylbenzyl)-3-(3-methylphenyl)propyl]-2,2-diethylpropane-1,3-diamide, N,N'-bis[(1S)-(1-naphthyl)-2-hydroxy-2-(4-methylbenzyl)-3-(4-methylphenyl)propyl]-2,2-diethylpropane-1,3-diamide, N,N'-bis[(1S)-(1-naphthyl)-2-hydroxy-2-(2-methoxybenzyl)-3-(2-methoxyphenyl)propyl]-2,2-diethylpropane-1,3-diamide, N,N'-bis[(1S)-(1-naphthyl)-2-hydroxy-2-(3-methoxybenzyl)-3-(3-methoxyphenyl)propyl]-2,2-diethylpropane-1,3-diamide, N,N'-bis[(1S)-(1-naphthyl)-2-hydroxy-2-(4-methoxybenzyl)-3-(4-methoxyphenyl)propyl]-2,2-diethylpropane-1,3-diamide, N,N'-bis[(1S)-(1-naphthyl)-2-hydroxy-2-(1-naphthylmethyl)-3-(1-naphthyl)propyl]-2,2-diethylpropane-1,3-diamide, N,N'-bis[(1S)-(1-naphthyl)-2-hydroxy-2-(2-naphthylmethyl)-3-(2-naphthyl)propyl]-2,2-diethylpropane-1,3-diamide, N,N'-bis[(1S)-(1-naphthyl)-2-hydroxy-2,2-diphenylethyl]-2,2-diethylpropane-1,3-diamide, N,N'-bis[(1S)-(1-naphthyl)-2-hydroxy-2,2-di(3-methyphenyl)ethyl]-2,2-diethylpropane-1,3-diamide, N,N'-bis[(1S)-(1-naphthyl)-2-hydroxy-2,2-di(4-methyphenyl)ethyl]-2,2-diethylpropane-1,3-diamide, N,N'-bis[(1S)-(1-naphthyl)-2-hydroxy-2,2-di(2-methoxyphenyl)ethyl]-2,2-diethylpropane-1,3-diamide, N,N'-bis[(1S)-(1-naphthyl)-2-hydroxy-2,2-di(3-methoxyphenyl)ethyl]-2,2-diethylpropane-1,3-diamide, N,N'-bis[(1S)-(1-naphthyl)(1-hydroxycyclopropyl)methyl]-2,2-diethylpropane-1,3-diamide, N,N'-bis[(1S)-(1-naphthyl)(1-hydroxycyclopentyl)methyl]-2,2-diethylpropane-1,3-diamide, N,N'-bis[(1S)-(1-naphthyl)-2-hydroxy-2-methylpropyl]-2,2-di(n-propyl)propane-1,3-diamide, N,N'-bis[(1S)-(1-naphthyl)-2-hydroxy-2-ethylbutyl]-2,2-di(n-propyl)propane-1,3-diamide, N,N'-bis[(1S)-(1-naphthyl)-2-hydroxy-2-n-propylpentyl]-2,2-di(n-propyl)propane-1,3-diamide, N,N'-bis[(1S)-(1-naphthyl)-2-hydroxy-2-n-butylhexyl]-2,2-di-(n-propyl)propane-1,3-diamide, N,N'-bis[(1S)-(1-naphthyl)-2-hydroxy-2-isobutyl-4-methylpentyl]-2,2-di(n-propyl)propane-1,3-diamide, N,N'-bis[(1S)-(1-naphthyl)-2-hydroxy-2-n-pentylheptyl]-2,2-di(n-propyl)propane-1,3-diamide, N,N'-bis[(1S)-(1-naphthyl)-2-hydroxy-2-n-hexyloctyl]-2,2-di(n-propyl)propane-1,3-diamide, N,N'-bis[(1S)-(1-naphthyl)-2-hydroxy-2-benzyl-3-phenylpropyl]-2,2-di(n-propyl)propane-1,3-diamide, N,N'-bis[(1S)-(1-naphthyl)-2-hydroxy-2-(2-methylbenzyl)-3-(2-methylphenyl)propyl]-2,2-di(n-propyl)propane-1,3-diamide, N,N'-bis[(1S)-(1-naphthyl)-2-hydroxy-2-(3-methylbenzyl)-3-(3-methylphenyl)propyl]-2,2-di(n-propyl)propane-1,3-diamide, N,N'-bis[(1S)-(1-naphthyl)-2-hydroxy-2-(4-methylbenzyl)-3-(4-methylphenyl)propyl]-2,2-di(n-propyl)propane-1,3-diamide, N,N'-bis[(1S)-(1-naphthyl)-2-hydroxy-2-(2-methoxybenzyl)-3-(2-methoxyphenyl)propyl]-2,2-di(n-propyl)propane-1,3-diamide, N,N'-bis[(1S)-(1-naphthyl)-2-hydroxy-2-(3-methoxybenzyl)-3-(3-methoxyphenyl)propyl]-2,2-di(n-propyl)propane-1,3-diamide, N,N'-bis[(1S)-(1-naphthyl)-2-hydroxy-2-(4-methoxybenzyl)-3-(4-methoxyphenyl)propyl]-2,2-di(n-propyl)propane-1,3-diamide, N,N'-bis[(1S)-(1-naphthyl)-2-hydroxy-2-(1-naphthylmethyl)-3-(1-naphthyl)propyl]-2,2-di(n-propyl)propane-1,3-diamide, N,N'-bis[(1S)-(1-naphthyl)-2-hydroxy-2-(2-naphthylmethyl)-3-(2-naphthyl)propyl]-2,2-di(n-propyl)propane-1,3-diamide, N,N'-bis[(1S)-(1-naphthyl)-2-hydroxy-2,2-diphenylethyl]-2,2-di(n-propyl)propane-1,3-diamide, N,N'-bis[(1S)-(1-naphthyl)-2-hydroxy-2,2-di(3-methyphenyl)ethyl]-2,2-di(n-propyl)propane-1,3-diamide, N,N'-bis[(1S)-(1-naphthyl)-2-hydroxy-2,2-di(4-methyphenyl)ethyl]-2,2-di(n-propyl)propane-1,3-diamide, N,N'-bis[(1S)-(1-naphthyl)-2-hydroxy-2,2-di(2-methoxyphenyl)ethyl]-2,2-di(n-propyl)propane-1,3-diamide, N,N'-bis[(1S)-(1-naphthyl)-2-hydroxy-2,2-di(3-methoxyphenyl)ethyl]-2,2-di(n-propyl)propane-1,3-diamide, N,N'-bis[(1S)-(1-naphthyl)(1-hydroxycyclopropyl)methyl]-2,2-di(n-propyl)propane-1,3-diamide, N,N'-bis[(1S)-(1-naphthyl)(1-hydroxycyclobutyl)methyl]-2,2-di(n-propyl)propane-1,3-diamide, N,N'-bis[(1S)-(1-naphthyl)(1-hydroxycyclopentyl)methyl]-2,2-di(n-propyl)propane-1,3-diamide, N,N'-bis[(1S)-(1-naphthyl)(1-hydroxycyclohexyl)methyl]-2,2-di(n-propyl)propane-1,3-diamide, N,N'-bis[(1S)-(1-naphthyl)(1-hydroxycycloheptyl)methyl]-2,2-di(n-propyl)propane-1,3-diamide, N,N'-bis[(1S)-(1-naphthyl)-2-hydroxy-2-methylpropyl]cyclopropane-1,1-dicarboxamide, N,N'-bis[(1S)-(1-naphthyl)-2-hydroxy-2-ethylbutyl]cyclopropane-1,1-dicarboxamide, N,N'-bis[(1S)-(1-naphthyl)-2-hydroxy-2-n-propylpentyl]cyclopropane-1,1-dicarboxamide, N,N'-bis[(1S)-(1-naphthyl)-2-hydroxy-2-n-butylhexyl]cyclopropane-1,1-dicarboxamide, N,N'-bis[(1S)-(1-naphthyl)-2-hydroxy-2-isobutyl-4-methylpentyl]cyclopropane-1,1-dicarboxamide, N,N'-bis[(1S)-(1-naphthyl)-2-hydroxy-2-n-pentylheptyl]cyclopropane-1,1-dicarboxamide, N,N'-bis[(1S)-(1-naphthyl)-2-hydroxy-2-n-hexyloctyl]cyclopropane-1,1-dicarboxamide, N,N'-bis[(1S)-(1-naphthyl)-2-hydroxy-2-benzyl-3-phenylpropyl]cyclopropane-1,1-dicarboxamide, N,N'-bis[(1S)-(1-naphthyl)-2-hydroxy-2-(2-methylbenzyl)-3-(2-methylphenyl)propyl]cyclopropane-1,1-dicarboxamide, N,N'-bis[(1S)-(1-naphthyl)-2-hydroxy-2-(3-methylbenzyl)-3-(3-methylphenyl)propyl]cyclopropane-1,1-dicarboxamide, N,N'-bis[(1S)-(1-naphthyl)-2-hydroxy-2-(4-methylbenzyl)-3-(4-methylphenyl)propyl]cyclopropane-1,1-dicarboxamide, N,N'-bis[(1S)-(1-naphthyl)-2-hydroxy-2-(2-methoxybenzyl)-3-(2-methoxyphenyl)propyl]cyclopropane-1,1-dicarboxamide, N,N'-bis[(1S)-(1-naphthyl)-2-hydroxy-2-(3-methoxybenzyl)-3-(3-methoxyphenyl)propyl]cyclopropane-1,1-dicarboxamide, N,N'-bis[(1S)-(1-naphthyl)-2-hydroxy-2-(4-methoxybenzyl)-3-(4-methoxyphenyl)propyl]cyclopropane-1,1-dicarboxamide, N,N'-bis[(1S)-(1-naphthyl)-2-hydroxy-2-(1-naphthylmethyl)-3-(1-naphthyl)propyl]cyclopropane-1,1-dicarboxamide, N,N'-bis[(1S)-(1-naphthyl)-2-hydroxy-2-(2-naphthylmethyl)-3-(2-naphthyl)propyl]cyclopropane-1,1-dicarboxamide, N,N'-bis[(1S)-(1-naphthyl)-2-hydroxy-2,2-diphenylethyl]cyclopropane-1,1-dicarboxamide, N,N'-bis[(1S)-(1-naphthyl)-2-hydroxy-2,2-di(3-methyphenyl)ethyl]cyclopropane-1,1-dicarboxamide, N,N'-bis[(1S)-(1-naphthyl)-2-hydroxy-2,2-di(4-methyphenyl)ethyl]cyclopropane-1,1-dicarboxamide, N,N'-bis[(1S)-(1-naphthyl)-2-hydroxy-2,2-di(2-methoxyphenyl)ethyl]cyclopropane-1,1-dicarboxamide, N,N'-bis[(1S)-(1- naphthyl)-2-hydroxy-2,2-di(3-methoxyphenyl)ethyl]cyclopropane-1,1-dicarboxamide, N,N'-bis[(1S)-(1-naphthyl)(1-hydroxycyclopropyl)methyl]cyclopropane-1,1-dicarboxamide, N,N'-bis[(1S)-(1-naphthyl)(1-hydroxycyclobutyl)methyl]cyclopropane-1,1-dicarboxamide, N,N'-bis[(1S)-(1-naphthyl)(1-hydroxycyclopentyl)methyl]cyclopropane-1,1-dicarboxamide, N,N'-bis[(1S)-(1-naphthyl)(1-hydroxycyclohexyl)methyl]cyclopropane-1,1-dicarboxamide, N,N'-bis[(1S)-(1-naphthyl)(1-hydroxycycloheptyl)methyl]cyclopropane-1,1-dicarboxamide, N,N'-bis[(1S)-(1-naphthyl)-2-hydroxy-2-methylpropyl]cyclobutane-1,1-dicarboxamide, N,N'-bis[(1S)-(1-naphthyl)-2-hydroxy-2-ethylbutyl]cyclobutane-1,1-dicarboxamide, N,N'-bis[(1S)-(1-naphthyl)-2-hydroxy-2-n-propylpentyl]cyclobutane-1,1-dicarboxamide, N,N'-bis[(1S)-(1-naphthyl)-2-hydroxy-2-n-butylhexyl]cyclobutane-1,1-dicarboxamide, N,N'-bis[(1S)-(1-naphthyl)-2-hydroxy-2-isobutyl-4-methylpentyl]cyclobutane-1,1-dicarboxamide, N,N'-bis[(1S)-(1-naphthyl)-2-hydroxy-2-n-pentylheptyl]cyclobutane-1,1-dicarboxamide, N,N'-bis[(1S)-(1-naphthyl)-2-hydroxy-2-n-hexyloctyl]cyclobutane-1,1-dicarboxamide, N,N'-bis[(1S)-(1-naphthyl)-2-hydroxy-2-benzyl-3-phenylpropyl]cyclobutane-1,1-dicarboxamide, N,N'-bis[(1S)-(1-naphthyl)-2-hydroxy-2-(2-methylbenzyl)-3-(2-methylphenyl)propyl]cyclobutane-1,1-dicarboxamide, N,N'-bis[(1S)-(1-naphthyl)-2-hydroxy-2-(3-methylbenzyl)-3-(3-methylphenyl)propyl]cyclobutane-1,1-dicarboxamide, N,N'-bis[(1S)-(1-naphthyl)-2-hydroxy-2-(4-methylbenzyl)-3-(4-methylphenyl)propyl]cyclobutane-1,1-dicarboxamide, N,N'-bis[(1S)-(1-naphthyl)-2-hydroxy-2-(2-methoxybenzyl)-3-(2-methoxyphenyl)propyl]cyclobutane-1,1-dicarboxamide, N,N'-bis[(1S)-(1-naphthyl)-2-hydroxy-2-(3-methoxybenzyl)-3-(3-methoxyphenyl)propyl]cyclobutane-1,1-dicarboxamide, N,N'-bis[(1S)-(1-naphthyl)-2-hydroxy-2-(4-methoxybenzyl)-3-(4-methoxyphenyl)propyl]cyclobutane-1,1-dicarboxamide, N,N'-bis[(1S)-(1-naphthyl)-2-hydroxy-2-(1-naphthylmethyl)-3-(1-naphthyl)propyl]cyclobutane-1,1-dicarboxamide, N,N'-bis[(1S)-(1-naphthyl)-2-hydroxy-2-(2-naphthylmethyl)-3-(2-naphthyl)propyl]cyclobutane-1,1-dicarboxamide, N,N'-bis[(1S)-(1-naphthyl)-2-hydroxy-2,2-diphenylethyl]cyclobutane-1,1-dicarboxamide, N,N'-bis[(1S)-(1-naphthyl)-2-hydroxy-2,2-di(3-methyphenyl)ethyl]cyclobutane-1,1-dicarboxamide, N,N'-bis[(1S)-(1-naphthyl)-2-hydroxy-2,2-di(4-methyphenyl)ethyl]cyclobutane-1,1-dicarboxamide, N,N'-bis[(1S)-(1-naphthyl)-2-hydroxy-2,2-di(2-methoxyphenyl)ethyl]cyclobutane-1,1-dicarboxamide, N,N'-bis[(1S)-(1-naphthyl)-2-hydroxy-2,2-di(3-methoxyphenyl)ethyl]cyclobutane-1,1-dicarboxamide, N,N'-bis[(1S)-(1-naphthyl)(1-hydroxycyclopropyl)methyl]cyclobutane-1,1-dicarboxamide, N,N'-bis[(1S)-(1-naphthyl)(1-hydroxycyclobutyl)methyl]cyclobutane-1,1-dicarboxamide, N,N'-bis[(1S)-(1-naphthyl)(1-hydroxycyclopentyl)methyl]cyclobutane-1,1-dicarboxamide, N,N'-bis[(1S)-(1-naphthyl)(1-hydroxycyclohexyl)methyl]cyclobutane-1,1-dicarboxamide, N,N'-bis[(1S)-(1-naphthyl)(1-hydroxycycloheptyl)methyl]cyclobutane-1,1-dicarboxamide, N,N'-bis[(1S)-(1-naphthyl)-2-hydroxy-2-methylpropyl]cyclopentane-1,1-dicarboxamide, N,N'-bis[(1S)-(1-naphthyl)-2-hydroxy-2-ethylbutyl]cyclopentane-1,1-dicarboxamide, N,N'-bis[(1S)-(1-naphthyl)-2-hydroxy-2-n-propylpentyl]cyclopentane-1,1-dicarboxamide, N,N'-bis[(1S)-(1-naphthyl)-2-hydroxy-2-n-butylhexyl]cyclopentane-1,1-dicarboxamide, N,N'-bis[(1S)-(1-naphthyl)-2-hydroxy-2-isobutyl-4-methylpentyl]cyclopentane-1,1-dicarboxamide, N,N'-bis[(1S)-(1-naphthyl)-2-hydroxy-2-n-pentylheptyl]cyclopentane-1,1-dicarboxamide, N,N'-bis[(1S)-(1-naphthyl)-2-hydroxy-2-n-hexyloctyl]cyclopentane-1,1-dicarboxamide, N,N'-bis[(1S)-(1-naphthyl)-2-hydroxy-2-benzyl-3-phenylpropyl]cyclopentane-1,1-dicarboxamide, N,N'-bis[(1S)-(1-naphthyl)-2-hydroxy-2-(2-methylbenzyl)-3-(2-methylphenyl)propyl]cyclopentane-1,1-dicarboxamide, N,N'-bis[(1S)-(1-naphthyl)-2-hydroxy-2-(3-methylbenzyl)-3-(3-methylphenyl)propyl]cyclopentane-1,1-dicarboxamide, N,N'-bis[(1S)-(1-naphthyl)-2-hydroxy-2-(4-methylbenzyl)-3-(4-methylphenyl)propyl]cyclopentane-1,1-dicarboxamide, N,N'-bis[(1S)-(1-naphthyl)-2-hydroxy-2-(2-methoxybenzyl)-3-(2-methoxyphenyl)propyl]cyclopentane-1,1-dicarboxamide, N,N'-bis[(1S)-(1-naphthyl)-2-hydroxy-2-(3-methoxybenzyl)-3-(3-methoxyphenyl)propyl]cyclopentane-1,1-dicarboxamide, N,N'-bis[(1S)-(1-naphthyl)-2-hydroxy-2-(4-methoxybenzyl)-3-(4-methoxyphenyl)propyl]cyclopentane-1,1-dicarboxamide, N,N'-bis[(1S)-(1-naphthyl)-2-hydroxy-2-(1-naphthylmethyl)-3-(1-naphthyl)propyl]cyclopentane-1,1-dicarboxamide, N,N'-bis[(1S)-(1-naphthyl)-2-hydroxy-2-(2-naphthylmethyl)-3-(2-naphthyl)propyl]cyclopentane-1,1-dicarboxamide, N,N'-bis[(1S)-(1-naphthyl)-2-hydroxy-2,2-diphenylethyl]cyclopentane-1,1-dicarboxamide, N,N'-bis[(1S)-(1-naphthyl)-2-hydroxy-2,2-di(3-methyphenyl)ethyl]cyclopentane-1,1-dicarboxamide, N,N'-bis[(1S)-(1-naphthyl)-2-hydroxy-2,2-di(4-methyphenyl)ethyl]cyclopentane-1,1-dicarboxamide, N,N'-bis[(1S)-(1-naphthyl)-2-hydroxy-2,2-di(2-methoxyphenyl)ethyl]cyclopentane-1,1-dicarboxamide, N,N'-bis[(1S)-(1-naphthyl)-2-hydroxy-2,2-di(3-methoxyphenyl)ethyl]cyclopentane-1,1-dicarboxamide, N,N'-bis[(1S)-(1-naphthyl)(1-hydroxycyclopropyl)methyl]cyclopentane-1,1-dicarboxamide, N,N'-bis[(1S)-(1-naphthyl)(1-hydroxycyclobutyl)methyl]cyclopentane-1,1-dicarboxamide, N,N'-bis[(1S)-(1-naphthyl)(1-hydroxycyclopentyl)methyl]cyclopentane-1,1-dicarboxamide, N,N'-bis[(1S)-(1-naphthyl)(1-hydroxycyclohexyl)methyl]cyclopentane-1,1-dicarboxamide, N,N'-bis[(1S)-(1-naphthyl)(1-hydroxycycloheptyl)methyl]cyclopentane-1,1-dicarboxamide, N,N'-bis[(1S)-(1-naphthyl)-2-hydroxy-2-methylpropyl]cyclohexane-1,1-dicarboxamide, N,N'-bis[(1S)-(1-naphthyl)-2-hydroxy-2-ethylbutyl]cyclohexane-1,1-dicarboxamide, N,N'-bis[(1S)-(1-naphthyl)-2-hydroxy-2-n-propylpentyl]cyclohexane-1,1-dicarboxamide, N,N'-bis[(1S)-(1-naphthyl)-2-hydroxy-2-n-butylhexyl]cyclohexane-1,1-dicarboxamide, N,N'-bis[(1S)-(1-naphthyl)-2-hydroxy-2-isobutyl-4-methylpentyl]cyclohexane-1,1-dicarboxamide, N,N'-bis[(1S)-(1-naphthyl)-2-hydroxy-2-n-pentylheptyl]cyclohexane-1,1-dicarboxamide, N,N'-bis[(1S)-(1-naphthyl)-2-hydroxy-2-n-hexyloctyl]cyclohexane-1,1-dicarboxamide, N,N'-bis[(1S)-(1-naphthyl)-2-hydroxy-2-benzyl-3-phenylpropyl]cyclohexane-1,1-dicarboxamide, N,N'-bis[(1S)-(1-naphthyl)-2-hydroxy-2-(2-methylbenzyl)-3-(2-methylphenyl)propyl]cyclohexane-1,1-dicarboxamide, N,N'-bis[(1S)-(1-naphthyl)-2-hydroxy-2-(3-methylbenzyl)-3-(3-methylphenyl)propyl]cyclohexane-1,1-dicarboxamide, N,N'-bis[(1S)-(1-naphthyl)-2-hydroxy-2-(4-methylbenzyl)-3-(4-methylphenyl)propyl]cyclohexane-1,1-dicarboxamide, N,N'-bis[(1S)-(1-naphthyl)-2-hydroxy-2-(2-methoxybenzyl)-3-(2-methoxyphenyl)propyl]cyclohexane-1,1-dicarboxamide, N,N'-bis[(1S)-(1-naphthyl)-2-hydroxy-2-(3-methoxybenzyl)-3-(3-methoxyphenyl)propyl]cyclohexane- 1,1-dicarboxamide, N,N'-bis[(1S)-(1-naphthyl)-2-hydroxy-2-(4-methoxybenzyl)-3-(4-methoxyphenyl)propyl]cyclohexane-1,1-dicarboxamide,
N,N'-bis[(1S)-(1-naphthyl)-2-hydroxy-2-(1-naphthylmethyl)-3-(1-naphthyl)propyl]cyclohexane-1,1-dicarboxamide, N,N'-bis[(1S)-(1-naphthyl)-2-hydroxy-2-(2-naphthylmethyl)-3-(2-naphthyl)propyl]cyclohexane-1,1-dicarboxamide, N,N'-bis[(1S)-(1-naphthyl)-2-hydroxy-2,2-diphenylethyl]cyclohexane-1,1-dicarboxamide, N,N'-bis[(1S)-(1-naphthyl)-2-hydroxy-2,2-di(3-methyphenyl)ethyl]cyclohexane-1,1-dicarboxamide, N,N'-bis[(1S)-(1-naphthyl)-2-hydroxy-2,2-di(4-methyphenyl)ethyl]cyclohexane-1,1-dicarboxamide, N,N'-bis[(1S)-(1-naphthyl)-2-hydroxy-2,2-di(2-methoxyphenyl)ethyl]cyclohexane-1,1-dicarboxamide, N,N'-bis[(1S)-(1-naphthyl)-2-hydroxy-2,2-di(3-methoxyphenyl)ethyl]cyclohexane-1,1-dicarboxamide, N,N'-bis[(1S)-(1-naphthyl)(1-hydroxycyclopropyl)methyl]cyclohexane-1,1-dicarboxamide, N,N'-bis[(1S)-(1-naphthyl)(1-hydroxycyclobutyl)methyl]cyclohexane-1,1-dicarboxamide, N,N'-bis[(1S)-(1-naphthyl)(1-hydroxycyclopentyl)methyl]cyclohexane-1,1-dicarboxamide, N,N'-bis[(1S)-(1-naphthyl)(1-hydroxycyclohexyl)methyl]cyclohexane-1,1-dicarboxamide, N,N'-bis[(1S)-(1-naphthyl)(1-hydroxycycloheptyl)methyl]cyclohexane-1,1-dicarboxamide; and these compounds in which 1-naphthyl group at the 1-position of the group bonded to the amido-nitrogen atom is replaced with 2-naphthyl group; and these compounds in which the configuration (1S) is changed to (1R).

As the Lewis acid, usually, non-protonic acids are used and examples thereof include titanium tetraalkoxides such as titanium tetraisopropoxide; titanium halides such as titanium chloride; aluminum tetraalkoxides such as aluminum tetraisopropoxide; aluminum halides such as aluminum chloride, ethyl aluminum dichloride, and diethyl aluminum chloride; trialkyl aluminum such as trimethyl aluminum and triethyl aluminum; tin halides such as dimethyl tin dichloride and tin chloride; zinc halides such as zinc chloride; alkoxy zinc such as diisopropoxy zinc; zirconium halides such as zirconium chloride; and hafnium halides such as hafnium chloride. These Lewis acids may be used alone or two or more thereof may be used in form of a mixture. The amount of the Lewis acid to be used is generally about 0.001 to 5 moles, preferably about 0.01 to 1 mole relative to 1 mole of the optically active diamide compound (2).

The optically active bisoxazoline compound (1) can be obtained by reacting the optically active diamide compound (2) with the Lewis acid and, usually, such process can be carried out in the presence of a solvent. The solvent is not particularly limited in so far as it is an inert solvent on the reaction and examples thereof include aromatic hydrocarbon solvents such as toluene and xylene; aliphatic hydrocarbon solvents such as heptane and octane; and halogenated hydrocarbon solvents such as chlorobenzene, dichloromethane, and dichloroethane. They may be used alone or in the form of a mixture. The amount of the solvent to be used is not particularly limited and it is generally about 2 to 200 parts by weight relative to 1 part by weight of the optically active diamide compound (2).

The reaction temperature for reacting the Lewis acid is usually about 50 to 250° C., preferably about 60 to 180° C. The reaction time is not particularly limited and the reaction can be terminated when it is found that the optically active diamide compound (2) disappears or the progress of the reaction ceases by analyzing the progress of the reaction by a conventional means such as gas chromatography, high performance liquid chromatography, and the like.

After completion of the reaction, the reaction mixture obtained is concentrated to obtain the optically active bisoxazoline compound (1). While the optically active bisoxazoline compound (1) thus obtained can be used as it is for producing an asymmetric copper complex as described hereinafter, preferably, it is used after purifying by a conventional purification means such as column chromatography, recrystallization, and the like. Further, the optically active bisoxazoline compound (1) can be isolated by mixing the reaction mixture with an aqueous alkaline solution such as an aqueous sodium hydrogen carbonate solution and, after removing insoluble matters by filtration if necessary, conducting extracting treatment, and concentrating the resulting organic layer.

The optically active diamide compound (2) can be obtained by reacting an optically active amino alcohol represented by the formula (3):

(3)

wherein $R^1$, $R^2$, $R^3$, and * are as defined above (hereinafter, simply referred to as the optically active amino alcohol (3)) and a malonic acid compound represented by the formula (4):

(4)

wherein $R^4$ and $R^5$ are as defined above and Z represents an alkoxy group or a halogen atom (hereinafter, simply referred to the malonic acid compound (4)).

Examples of the optically active amino alcohol (3) include (R)-1-amino-1-(1-naphthyl)-2-methyl-2-propanol, (R)-1-amino-1-(1-naphthyl)-2-ethyl-2-butanol, (R)-1-amino-1-(1-naphthyl)-2-n-propyl-2-pentanol, (R)-1-amino-1-(1-naphthyl)-2-n-butyl-2-hexanol, (R)-1-amino-1-(1-naphthyl)-2-isobutyl-4-methyl-2-pentanol, (R)-1-amino-1-(1-naphthyl)-2-n-pentyl-2-heptanol, (R)-1-amino-1-(1-naphthyl)-2-n-hexyl-2-octanol, (R)-1-amino-1-(1-naphthyl)-2-benzyl-3-phenyl-2-propanol, (R)-1-amino-1-(1-naphthyl)-2-(3-methylbenzyl)-3-(3-methylphenyl)-2-propanol, (R)-1-amino-1-(1-naphthyl)-2-(2-methylbenzyl)-3-(2-methylphenyl)-2-propanol, (R)-1-amino-1-(1-naphthyl)-2-(4-methylbenzyl)-3-(4-methylphenyl)-2-propanol, (R)-1-amino-1-(1-naphthyl)-2-(2-methoxybenzyl)-3-(2-methoxyphenyl)-2-propanol, (R)-1-amino-1-(1-naphthyl)-2-(3-methoxybenzyl)-3-(3-methoxyphenyl)-2-propanol, (R)-1-amino-1-(1-naphthyl)-2-(4-methoxybenzyl)-3-(4-methoxyphenyl)-2-propanol, (R)-1-amino-1-(1-naphthyl)-2-(1-naphthylmethyl)-3-(1-naphthyl)-2-propanol, (R)-1-amino-1-(1-naphthyl)-2-(2-naphthylmethyl)-3-(2-naphthyl)-2-propanol, (R)-2-amino-2-(1-naphthyl)-1,1-diphenylethanol, (R)-2-amino-2-(1-naphthyl)-1,1-di(3-methylphenyl)ethanol, (R)-2-amino-2-

(1-naphthyl)-1,1-di(4-methylphenyl)ethanol, (R)-2-amino-2-(1-naphthyl)-1,1-di(2-methoxyphenyl)ethanol, (R)-2-amino-2-(1-naphthyl)-1,1-di(3-methoxyphenyl)ethanol, (R)-2-amino-2-(1-naphthyl)-1,1-di(4-methoxyphenyl)ethanol, 1-[(R)-amino-(1-naphthyl)methyl]cyclopropanol, 1-[(R)-amino-(1-naphthyl)methyl]cyclobutanol, 1-[(R)-amino-(1-naphthyl)methyl]cyclopentanol, 1-[(R)-amino-(1-naphthyl)methyl]cyclohexanol, 1-[(R)-amino-(1-naphthyl)methyl]cycloheptanol, (R)-1-amino-1-(2-naphthyl)-2-methyl-2-propanol, (R)-1-amino-1-(2-naphthyl)-2-ethyl-2-butanol, (R)-1-amino-1-(2-naphthyl)-2-n-propyl-2-pentanol, (R)-1-amino-1-(2-naphthyl)-2-n-butyl-2-hexanol, (R)-1-amino-1-(2-naphthyl)-2-isobutyl-4-methyl-2-pentanol, (R)-1-amino-1-(2-naphthyl)-2-n-pentyl-2-heptanol, (R)-1-amino-1-(2-naphthyl)-2-n-hexyl-2-octanol, (R)-1-amino-1-(2-naphthyl)-2-benzyl-3-phenyl-2-propanol, (R)-1-amino-1-(2-naphthyl)-2-(3-methylbenzyl)-3-(3-methylphenyl)-2-propanol, (R)-1-amino-1-(2-naphthyl)-2-(2-methylbenzyl)-3-(2-methylphenyl)-2-propanol, (R)-1-amino-1-(2-naphthyl)-2-(4-methylbenzyl)-3-(4-methylphenyl)-2-propanol, (R)-1-amino-1-(2-naphthyl)-2-(2-methoxybenzyl)-3-(2-methoxyphenyl)-2-propanol, (R)-1-amino-1-(2-naphthyl)-2-(3-methoxybenzyl)-3-(3-methoxyphenyl)-2-propanol, (R)-1-amino-1-(2-naphthyl)-2-(4-methoxybenzyl)-3-(4-methoxyphenyl)-2-propanol, (R)-1-amino-1-(2-naphthyl)-2-(1-naphthylmethyl)-3-(1-naphthyl)-2-propanol, (R)-1-amino-1-(2-naphthyl)-2-(2-naphthylmethyl)-3-(2-naphthyl)-2-propanol, (R)-2-amino-2-(2-naphthyl)-1,1-diphenylethanol, (R)-2-amino-2-(2-naphthyl)-1,1-di(3-methylphenyl)ethanol, (R)-2-amino-2-(2-naphthyl)-1,1-di(4-methylphenyl)ethanol, (R)-2-amino-2-(2-naphthyl)-1,1-di(2-methoxyphenyl)ethanol, (R)-2-amino-2-(2-naphthyl)-1,1-di(3-methoxyphenyl)ethanol, (R)-2-amino-2-(2-naphthyl)-1,1-di(4-methoxyphenyl)ethanol, 1-[(R)-amino-(2-naphthyl)methyl]cyclopropanol, 1-[(R)-amino-(2-naphthyl)methyl]cyclobutanol, 1-[(R)-amino-(2-naphthyl)methyl]cyclopentanol, 1-[(R)-amino-(2-naphthyl)methyl]cyclohexanol, 1-[(R)-amino-(2-naphthyl)methyl]cycloheptanol, and these compounds wherein the configuration (R) is changed to (S). Such the optically active amino alcohol (3) may be acid added salts such as hydrochloride, sulfate, and acetate.

The optically active amino alcohol (3) can be produced by optical resolution of an amino alcohol compound as described hereinafter or by reaction of a corresponding optically active amino acid ester with a corresponding Grignard reagent. The optically active amino acid ester can be obtained by esterifying an optically active amino acid, which can be obtained by a method described in Tetrahedron 55(1999)11295-11308, by a known method or the method described hereinafter. Further, if necessary, the amino group of the optically active amino acid ester can be protected with a suitable protective group and, after the reaction with a Grignard reagent, it can be deprotected.

In the formula of the malonic acid compound (4), Z represents an alkoxy group or a halogen atom. Examples of the alkoxy include an alkoxy group having 1 to 6 carbon atoms such as a methoxy, ethoxy, n-propoxy, isopropoxy, n-butoxy, isobutoxy, pentyloxy, and hexyloxy group. Examples of the halogen atom include a chlorine and bromine atom.

Examples of the malonic acid compound (4) include malonic acid diesters such as dimethyl malonate, diethyl malonate, dimethyl dimethylmalonate, dimethyl diethylmalonate, dimethyl di(n-propyl)malonate, dimethyl 1,1-cyclopropanedicarboxylate, dimethyl 1,1-cyclobutanedicarboxylate, dimethyl 1,1-cyclopentanedicarboxylate, and dimethyl 1,1-cyclohexanedicarboxylate; and malonic acid halides such as malonic acid dichloride, dimethylmalonic acid dichloride, diethylmalonic acid dichloride, di(n-propyl)malonic acid dichloride, 1,1-dichloropropanedicarboxylic acid dichloride, 1,1-cyclobutanedicarboxylic acid dichloride, 1,1-cyclopentanedicarboxylic acid dichloride, 1,1-cyclohexanedicarboxylic acid dichloride, and malonic acid dibromide.

The amount of the malonic acid compound (4) to be used is usually about 0.3 to 2 moles, preferably about 0.5 to 1 mole relative to 1 mole of the optically active amino alcohol (3).

The reaction of the optically active amino alcohol (3) and the malonic acid compound (4) is usually carried out by mixing and bringing both into contact with each other in the presence of a solvent. The solvent to be used is not particularly limited in so far as it is an inert solvent on the reaction and examples thereof include the same solvent as that exemplified above with respect to the reaction of the optically active diamide compound (2) and the Lewis acid.

The reaction temperature in case of using a malonic acid diester in which Z is an alkoxy group as the malonic acid compound (4) is usually about 50 to 250° C., preferably about 60 to 180° C. In this case, the reaction may be carried out in the presence of a catalyst such as a lithium compound. Examples of the lithium compound include lithium alkoxides such as lithium methoxide and lithium ethoxide; lithium halide such as lithium chloride; and lithium hydroxide. The amount of the catalyst to be used is not particularly limited and it is usually about 0.0005 to 0.5 mole relative to 1 mole of the diamide compound (2).

The reaction temperature in case of using a malonic acid halide in which Z is a halogen atom as the malonic acid compound (4) is usually about −30 to 100° C., preferably about −10 to 50° C. In this case, for trapping the by-product, a hydrogen halide, preferably, the reaction is carried out in the presence of a base such as triethylamine.

The reaction of the optically active amino alcohol (3) and the malonic acid compound (4) gives the optically active diamide compound (2), and the optically active diamide compound (2) can be isolated by adding water to the reaction mixture to conduct extracting treatment, followed by concentrating the resulting organic layer. Further, the reaction mixture containing the optically active diamide compound (2) obtained as such may be contacted with the above-mentioned Lewis acid to produce the optically active bisoxazoline compound (1).

Next, the following description will illustrate the process for producing an optically active cyclopropane compound represented by the formula (7):

wherein $R^6$, $R^7$, $R^8$, and $R^9$ are the same or different and independently represent a hydrogen atom, an alkyl group optionally substituted with a halogen atom, an alkenyl group optionally substituted with a halogen atom, a substituted or unsubstituted aryl or aralkyl group, provided that, when $R^6$ and $R^8$ are the same, $R^6$ and $R^7$ are different from each other; and $R^{10}$ represents an alkyl group having 1 to 6 carbon atoms (hereinafter, simply referred to as the optically active cyclopropane compound (7)) by reaction of a prochiral olefin represented by the formula (5):

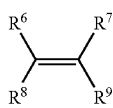

(5)

wherein $R^6$, $R^7$, $R^8$, and $R^9$ are as defined above (hereinafter, simply referred to as the olefin (5)), and a diazoacetic acid ester represented by the formula (6):

(6)

wherein $R^{10}$ is as defined above (hereinafter, simply referred to as the diazoacetic acid ester (6)) in the presence of a novel asymmetric copper complex produced from the optically active bisoxazoline compound (1) of the present invention and a copper compound.

The optically active bisoxazoline compound (1) has, as described above, two asymmetric carbon atoms and, usually, the compound in which both asymmetric carbon atoms are in the (S) configuration, or in the (R) configuration is used. They are suitably selected according to the desired optically active compound in an asymmetric synthesis reaction carried out using the compound as a catalyst or a catalytic component.

As the copper compound, monovalent or divalent copper compounds can be exemplified and specific examples include cuprous trifluoromethanesulfonate, cupric trifluoromethanesulfonate, cuprous acetate, cupric-acetate, cuprous bromide, cupric bromide, cuprous chloride, cupric chloride, and tetrakisacetonitrile copper(I) hexafluorophosphate, and among them, cuprous trifluoromethanesulfonate is preferable. The copper compounds can be used alone or two or more thereof can be used in the form of a mixture.

The amount of the optically active bisoxazoline compound (1) to be used is usually about 0.8 to 5 moles, preferably about 0.9 to 2 moles relative to 1 mole of the copper compound.

The optically active bisoxazoline compound (1) and the copper compound are brought into contact with each other usually in the presence of a solvent to produce the novel asymmetric copper complex. Examples of the solvent include halogenated hydrocarbons such as dichloromethane, dichloroethane, chloroform, and tetrachloromethane; and aromatic hydrocarbons such as benzene, toluene, and xylene. Also, when the olefin (5) is a liquid, the olefin (5) can be used as the solvent. The amount of the solvent to be used is usually about 10 to 500 parts by weight relative to 1 part by weight of the copper compound.

The preparation of the asymmetric copper complex is usually carried out in an atmosphere of an inert gas as argon gas or nitrogen gas and the preparation temperature is usually about 0 to 100° C.

The asymmetric copper complex can be prepared by brining the optically active bisoxazoline compound (1) and the copper compound into contact with each other and the asymmetric copper complex thus prepared can be isolated from the reaction mixture to be used for the reaction of the olefin (5) and diazoacetic acid ester (6), or can be used as such in the form of the reaction mixture without isolation.

Examples of the alkyl group optionally substituted with a halogen atom in the formula of the olefin (5) include a $C_{1-6}$ alkyl such as a methyl, ethyl, n-propyl, isopropyl, n-butyl, isobutyl, tert-butyl, n-pentyl, and hexyl group, and these alkyl groups whose one or more hydrogen atoms are substituted with halogen atoms such as a chloromethyl, fluoromethyl, trifluoromethyl, and chloroethyl group. Examples of the alkenyl group optionally substituted with a halogen atom include a $C_{2-6}$ alkenyl such as a vinyl, 1-propenyl, 2-propenyl, 2-methyl-1-propenyl, 1-butenyl, 2-butenyl, 3-butenyl, 2-pentenyl, and 2-hexenyl group and these alkenyl groups whose one or more hydrogen atoms are substituted with halogen atoms such as a 1-chloro-2-propenyl.

Examples of the substituted or unsubstituted aryl group include an unsubstituted aryl group (phenyl or naphthyl) and an aryl group substituted with an alkyl or alkoxy group, such as a phenyl, 1-naphthyl, 2-naphthyl, 2-methylphenyl, 4-methylphenyl, and 3-methoxyphenyl group. Examples of the substituted or unsubstituted aralkyl group include alkyl substituted with the above substituted or unsubstituted aryl group. Specific examples include a benzyl, 2-methylbenzyl, 4-methylbenzyl, 3-methoxybenzyl, 1-naphthylmethyl, and 2-naphthylmethyl group.

Examples of the olefin (5) include propene, 1-butene, isobutylene, 1-pentene, 1-hexene, 1-octene, 4-chloro-1-butene, 2-pentene, 2-heptene, 2-methyl-2-butene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 2-methyl-2,4-hexadiene, 1-fluoro-1,1-dichloro-4-methyl-2-pentene, 1,1,1-trichloro-4-methyl-3-pentene, 1,1,1-tribromo-4-methyl-3-pentene, 2,3-dimethyl-2-pentene, 2-methyl-3-phenyl-2-butene, 2-bromo-2,5-dimethyl-4-hexene, 2-chloro-2,5-dimethyl-4-hexene, and 2,5-dimethyl-6-chloro-2,4-hexadiene.

As the $C_{1-6}$ alkyl group in the formula of diazoacetic acid ester (6), there are, for example, the same groups as those exemplified above, and examples of the diazoacetic acid ester (6) include ethyl diazoacetate, n-propyl diazoacetate, isopropyl diazoacetate, n-butyl diazoacetate, isobutyl diazoacetate, tert-butyl diazoacetate, pentyl diazoacetate, and hexyl diazoacetate.

The amount of the asymmetric copper complex to be used is usually about 0.0001 to 0.05 mole, preferably 0.0005 to 0.01 mole in terms of the copper metal (mole of copper) relative to the diazoacetic acid ester (6).

The amount of the olefin (5) to be used is usually about 1 mole or more, preferably 1.2 moles or more relative to 1 mole of the diazoacetic acid ester (6). There is no specific upper limit and, when the olefin (5) is a liquid, large excess thereof can be used also to serve as the solvent.

The reaction of the olefin (5) and the diazoacetic acid ester (6) is usually carried out by bringing three components, the asymmetric copper complex, the olefin (5), and the diazoacetic acid ester (6), into contact with one another and mixing them, and the mixing order is not particularly limited. Usually, the diazoacetic acid ester (6) is added to a mixture of the asymmetric copper complex and the olefin (5). The reaction is usually carried out in the presence of a solvent, and examples of the solvent include halogenated hydrocarbon solvents such as dichloromethane, dichloroethane, chloroform, and tetrachloromethane; aliphatic hydrocarbons such as hexane, heptane, and cyclohexane; aromatic hydrocarbons such as benzene, toluene, and xylene; and esters such as ethyl acetate. They can be used alone or in the form of a mixed solvent. Although the amount to be used is not particularly limited, in view of the volume efficiency and the properties of the reaction mixture, the amount is usually about 2 to 30 parts by weight, preferably 5 to 20 parts by weight relative to 1 part by weight of the diazoacetic acid ester (6). The solvent can be mixed previously with the olefin (5), the diazoacetic acid ester (6), and/or the asymmetric copper complex. Alternatively, as described above, when the olefin (5) is a liquid, the olefin (5) can also be used as the solvent.

The reaction of the olefin (5) and the diazoacetic acid ester (6) is usually carried out in an atmosphere of an inert gas such as argon gas or nitrogen gas. Since water adversely affects the reaction, preferably, the reaction is carried out with suppressing the amount of water present in the reaction system by, for example, carrying out the reaction in the presence of a dehydrating agent in the reaction system, or using the olefin (5) or the solvent previously subjected to dehydration treatment.

The reaction temperature is usually about −50 to 150° C., preferably −20 to 80° C.

After completion of the reaction, the optically active cyclopropane compound (7) can be isolated by, for example, concentrating the reaction mixture. The isolated optically active cyclopropane compound (7) can further be purified by a conventional purification means such as distillation, column chromatography, and the like.

Examples of the optically active cyclopropane compound (7) include optically active methyl 2-methylcyclopropanecarboxylate, optically active methyl 2,2-dimethylcyclopropanecarboxylate, optically active methyl 2,2-dimethyl-3-(2-methyl-1-propenyl)cyclopropanecarboxylate, optically active methyl 2,2-dimethyl-3-(2,2-dichloro-1-ethenyl)cyclopropanecarboxylate, optically active methyl 2,2-dimethyl-3-(2,2,2-trichloroethyl)cyclopropanecarboxylate, optically active methyl 2,2-dimethyl-3-(2,2,2-tribromoethyl)cyclopropanecarboxylate, optically active methyl 2,2-dimethyl-3-(2,2-dibromo-1-ethenyl)cyclopropanecarboxylate, optically active methyl 2,2-dimethyl-3-(2,2-difluoro-1-ethenyl)cyclopropanecarboxylate, optically active methyl 2,2-dimethyl-3-(2-fluoro-2-chloro-1-ethenyl)cyclopropanecarboxylate, optically active methyl 2,2-dimethyl-3-(2-fluoro-2-bromo-1-ethenyl)cyclopropanecarboxylate, optically active methyl 2,2-dimethyl-3-(2-fluoro-1-propenyl)cyclopropanecarboxylate, optically active methyl 2,2-dimethyl-3-(2-chloro-1-propenyl)cyclopropanecarboxylate, optically active methyl 2,2-dimethyl-3-(2-chloro-2,2,2-trifluoromethylethenyl)cyclopropanecarboxylate, optically active methyl 2,2-dimethyl-3-(2-methoxycarbonyl-1-propenyl)cyclopropanecarboxylate, optically active methyl 2,2-dimethyl-3-(2-chloro-2-methyl)propylcyclopropanecarboxylate, optically active methyl 2,2-dimethyl-3-(2-bromo-2-methyl)propylcyclopropanecarboxylate, and optically active methyl 2,2-dimethyl-3-(1-propenyl)propylcyclopropanecarboxylate; and compounds wherein the above methyl ester moieties are replaced with ethyl, n-propyl, isopropyl, isobutyl and tert-butyl ester moieties.

The optically active cyclopropane compound (7) can be converted into an optically active cyclopropanecarboxylic acid in which $R^{10}$ is a hydrogen atom by hydrolysis according to a known hydrolysis method.

The optically active amino alcohol represented by the formula (3) includes an optically active amino alcohol represented by the following formula (30):

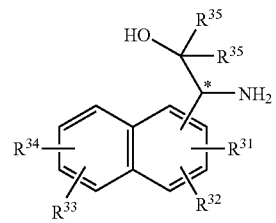

(30)

wherein $R^{31}$, $R^{32}$, $R^{33}$, and $R^{34}$ are the same or different and independently represent a hydrogen atom, a $C_{1-6}$ alkyl group, or a $C_{1-6}$ alkoxy group; $R^{35}$ represents a $C_{1-6}$ alkyl group, a substituted or unsubstituted phenyl group or a substituted or unsubstituted aralkyl group, or two $R^{35}$ together with the carbon atom to which they are bonded form a ring; * represents an asymmetric carbon atom (hereinafter, simply referred to as the optically active amino alcohol (30)). The following description will illustrate the compound.

In the formula (30), examples of the $C_{1-6}$ alkyl group represented by $R^{31}$ to $R^{35}$ include a straight or branched chain alkyl group such as a methyl, ethyl, n-propyl, isopropyl, n-butyl, isobutyl, sec-butyl, tert-butyl, pentyl, and n-hexyl group. Examples of the $C_{1-6}$ alkoxy group represented by $R^{31}$ to $R^{34}$ include a straight or branched chain alkoxy group such as a methoxy, ethoxy, n-propoxy, isopropoxy, n-butoxy, isobutoxy, tert-butoxy, pentyloxy, and n-hexyloxy group.

As the substituted or unsubstituted phenyl group represented by $R^{35}$, there is, for example, an unsubstituted phenyl group and, as the substituted phenyl group, there are, for example, a phenyl group substituted with the above exemplified $C_{1-6}$ alkyl group such as a 3-methylphenyl and 4-methylphenyl group and a phenyl group substituted with the above exemplified $C_{1-6}$ alkoxy group such as a 2-methoxyphenyl, 3-methoxyphenyl and 4-methoxyphenyl group. As the substituted or unsubstituted aralkyl group, there are, for example, a $C_{1-6}$ alkyl group substituted with an aryl group such as the above exemplified substituted or unsubstituted phenyl and naphthyl group. Specific examples thereof include a benzyl, 2-methylbenzyl, 3-methylbenzyl, 4-methylbenzyl, 2-methoxybenzyl, 3-methoxybenzyl, 4-methoxybenzyl, 1-naphthylmethyl, and 2-naphthylmethyl group.

Further, in case that two $R^{35}$ together with the carbon atom to which they are bonded form a ring, specific examples of the ring include rings having 3 to 7 carbon atoms such as a cyclopropane ring, cyclopentane ring, cyclohexyl ring, and cycloheptane ring.

Examples of the optically active amino alcohol (30) include (R)-1-amino-1-(1-naphthyl)-2-methyl-2-propanol, (R)-1-amino-1-(4-fluoro-1-naphthyl)-2-methyl-2-propanol, (R)-1-amino-1-(2-methyl-1-naphthyl)-2-methyl-2-propanol, (R)-1-amino-1-(4-methyl-1-naphthyl)-2-methyl-2-propanol, (R)-1-amino-1-(2-methoxy-1-naphthyl)-2-methyl-2-propanol, (R)-1-amino-1-(2-ethoxy-1-naphthyl)-2-methyl-2-propanol, (R)-1-amino-1-(4-methoxy-1-naphthyl)-2-methyl-2-propanol, (R)-1-amino-1-(2,4-dimethoxy-1-naphthyl)-2-methyl-2-propanol, (R)-1-amino-1-(2-naphthyl)-2-methyl-2-propanol, (R)-1-amino-1-(7- methyl-2-naphthyl)-2-methyl-2-propanol, (R)-1-amino-1-(1-n-propyl-2-naphthyl)-2-methyl-2-propanol, (R)-1-amino-1-(6-methoxy-2-naphthyl)-2-methyl-2-propanol, and (R)-1-amino-1-(3,8-dimethoxy-2-naphthyl)-2-methyl-2-propanol; and these compounds in which 2-methyl-2-propanol moieties are replaced with 2-ethyl-2-butanol, 2-n-propyl-2-pentanol, 2-n-butyl-2-hexanol, 2-isobutyl-4-methyl-2-pentanol, 2-n-pentyl-2-heptanol, 2-benzyl-3-phenyl-2-propanol, 2-(3-methylbenzyl)-3-(3-methylphenyl)-2-propanol, 2-(2-methylbenzyl)-3-(2-methylphenyl)-2-propanol, 2-(4-methylbenzyl)-3-(4-methylphenyl)-2-propanol, 2-(2-methoxybenzyl)-3-(2-methoxyphenyl)-2-propanol, 2-(3-methoxybenzyl)-3-(3-methoxyphenyl)-2-propanol, 2-(4-methoxybenzyl)-3-(4-methoxyphenyl)-2-propanol, 2-(1-naphthylmethyl)-3-(1-naphthyl)-2-propanol, and 2-(2-naphthylmethyl)-3-(2-naphthyl)-2-propanol.

Further, examples thereof also include (R)-2-amino-2-(1-naphthyl)-1,1-diphenylethanol, (R)-2-amino-2-(1-naphthyl)-1,1-di(3-methylphenyl)ethanol, (R)-2-amino-2-(1-naphthyl)-1,1-di(4-methylphenyl)ethanol, (R)-2-amino-2-(1-naphthyl)-1,1-di(2-methoxyphenyl)ethanol, (R)-2-amino-2-(1-naphthyl)-1,1-di(3-methoxyphenyl)ethanol, (R)-2-amino-2-(1-naphthyl)-1,1-di(4-methoxyphenyl)ethanol, 1-[(R)-amino-(1-naphthyl)methyl]cyclopropanol, 1-[(R)-amino-(1-naphthyl)methyl]cyclopentanol, and 1-[(R)-amino-(1-naphthyl)methyl]cycloheptanol; and these compounds in which the 1-naphthyl group bonded to the carbon atom to which the amino group is bonded is replaced with a 4-fluoro-1-naphthyl, 2-methyl-1-naphthyl, 4-methyl-1-naphthyl, 2-methoxy-1-naphthyl, 2-ethoxy-1-naphthyl, 4-methoxy-1-naphthyl, 2,4-dimethoxy-1-naphthyl, 2-naphthyl, 7-methyl-2-naphthyl, 1-n-propyl-2-naphthyl, 6-methoxy-2-naphthyl, and 3,8-dimethoxy-2-naphthyl group.

Further, these compounds in which (R) configuration is changed to (S) configuration are also exemplified.

The optically active amino alcohol (30) can be produced by optical resolution of a naphthyl alcohol represented by the following formula (40):

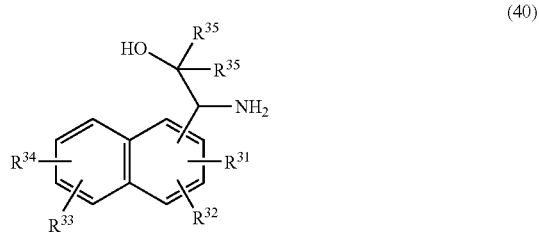

(40)

wherein $R^{31}$ $R^{32}$, $R^{33}$ $R^{34}$ and $R^{35}$ are as defined above (hereinafter, simply referred to as the naphthyl alcohol (40)), by an optically active N-formylphenylalanine.

Examples of the amino alcohol (40) include 1-amino-1-(1-naphthyl)-2-methyl-2-propanol, 1-amino-1-(4-fluoro-1-naphthyl)-2-methyl-2-propanol, 1-amino-1-(2-methyl-1-naphthyl)-2-methyl-2-propanol, 1-amino-1-(4-methyl-1-naphthyl)-2-methyl-2-propanol, 1-amino-1-(2-methoxy-1-naphthyl)-2-methyl-2-propanol, 1-amino-1-(2-ethoxy-1-naphthyl)-2-methyl-2-propanol, 1-amino-1-(4-methoxy-1-naphthyl)-2-methyl-2-propanol, 1-amino-1-(2,4-dimethoxy-1-naphthyl)-2-methyl-2-propanol, 1-amino-1-(2-naphthyl)-2-methyl-2-propanol, 1-amino-1-(7-methyl-2-naphthyl)-2-methyl-2-propanol, 1-amino-1-(1-n-propyl-2-naphthyl)-2-methyl-2-propanol, 1-amino-1-(6-methoxy-2-naphthyl)-2-methyl-2-propanol, and 1-amino-1-(3,8-dimethoxy-1-naphthyl)-2-methyl-2-propanol; and these compounds in which 2-methyl-2-propanol moieties are replaced with 2-ethyl-2-butanol, 2-n-propyl-2-pentanol, 2-n-butyl-2-hexanol, 2-isobutyl-4-methyl-2-pentanol, 2-n-pentyl-2-heptanol, 2-benzyl-3-phenyl-2-propanol, 2-(3-methylbenzyl)-3-(3-methylphenyl)-2-propanol, 2-(2-methylbenzyl)-3-(2-methylphenyl)-2-propanol, 2-(4-methylbenzyl)-3-(4-methylphenyl)-2-propanol, 2-(2-methoxybenzyl)-3-(2-methoxyphenyl)-2-propanol, 2-(3-methoxybenzyl)-3-(3-methoxyphenyl)-2-propanol, 2-(4-methoxybenzyl)-3-(4-methoxyphenyl)-2-propanol, 2-(1-naphthylmethyl)-3-(1-naphthyl)-2-propanol, and 2-(2-naphthylmethyl)-3-(2-naphthyl)-2-propanol.

Examples thereof also include 2-amino-2-(1-naphthyl)-1,1-diphenylethanol, 2-amino-2-(1-naphthyl)-1,1-di(3-methylphenyl)ethanol, 2-amino-2-(1-naphthyl)-1,1-di(4-methylphenyl)ethanol, 2-amino-2-(1-naphthyl)-1,1-di(2-methoxyphenyl)ethanol, 2-amino-2-(1-naphthyl)-1,1-di(3-methoxyphenyl)ethanol, 2-amino-2-(1-naphthyl)-1,1-di(4-methoxyphenyl)ethanol, 1-[(amino)-(1-naphthyl)methyl]cyclopropanol, 1-[(amino)-(1-naphthyl)methyl]cyclopentanol, and 1-[(amino)-(1-naphthyl)methyl]cycloheptanol; and these compounds in which the 1-naphthyl group bonded to the carbon atom to which the amino group is bonded is replaced with a 4-fluoro-1-naphthyl, 2-methyl-1-naphthyl, 4-methyl-1-naphthyl, 2-methoxy-1-naphthyl, 2-ethoxy-1-naphthyl, 4-methoxy-1-naphthyl, 2,4-dimethoxy-1-naphthyl, 2-naphthyl, 7-methyl-2-naphthyl, 1-n-propyl-2-naphthyl, 6-methoxy-2-naphthyl, and 3,8-dimethoxy-2-naphthyl group.

As the amino alcohol (40), usually, a racemic body can be used, while a mixture of optical isomers with a low optical purity in which one of optical isomers exists relatively in excess than the other may also be used.

The optically active N-formylphenylalanine has two kinds of optical isomers of R isomer and S isomer, and they can be suitably selected according to the desired optically active amino alcohols. The amount to be used is usually 0.1 to 1 mole relative to 1 mole of the amino alcohol (40).

The reaction of the amino alcohol (40) and the optically active N-formylphenylalanine is usually carried out by mixing both of them in a solvent and the mixing order is not particularly limited. It is preferable to add the optically active N-formylphenylalanine to a solution of the amino alcohol (40) in a solvent. The optically active N-formylphenylalanine can be added continuously or intermittently. Further, the optically active N-formylphenylalanine can be used as such or in the form of a solution in a solvent.

Examples of the solvent include aromatic hydrocarbon solvents such as toluene, xylene and chlorobenzene; ether solvents such as diethyl ether, methyl tert-butyl ether, tetrahydrofuran, dioxane, and dimethoxyethane; alcohol solvents such as methanol, ethanol, and isopropanol; ester solvents such as ethyl acetate; nitrile solvents such as acetonitrile; and water. They can be used alone or in the form of a mixed solvent. Among these solvents, ether solvents, alcohol solvents, and a mixed solvent thereof with water are preferable. The amount of the solvent to be used is usually 0.5 to 100 parts by weight, preferably 1 to 50 parts by weight relative to 1 part by weight of the amino alcohol (40). The solvent can be added previously to the amino alcohol or the optically active N-formylphenylalanine.

The reaction temperature is usually in a range of 0° C. to a refluxing temperature of the reaction mixture.

After completion of the reaction, the diastereomeric salts of the optically active N-formylphenylalanine and the optically active amino alcohol (30) (hereinafter, simply referred to as the diastereomeric salt) is formed and, usually, a part of one diastereomeric salt is precipitated in the reaction mass. This can be isolated as such, and preferably by cooling or concentrating the reaction mass to precipitate a much more amount of the diastereomeric salt. Depending on the conditions, the diastereomeric salt is completely dissolved in the reaction mass and in this case, the reaction mass can be cooled or concentrated to crystallize and isolate the diastereomeric salt. One diastereomeric salt precipitated can be isolated easily by conventional filtration. The isolated diastereomeric salt can be further purified by, for example, recrystallization treatment.

Examples of the diastereomeric salt thus obtained include the diastereomeric salt of optically active 1-amino-(1-naphthyl)-2-methyl-2-propanol and optically active N-formylphenylalanine; the diastereomeric salt of optically active 1-amino-1-(4-fluoro-1-naphthyl)-2-methyl-2-propanol and optically active N-formylphenylalanine; the diastereomeric salt of optically active 1-amino-1-(2-methyl-1-naphthyl)-2-methyl-2-propanol and optically active N-formylphenylalanine; the diastereomeric salt of optically active 1-amino-1-(4-methyl-1-naphthyl)-2-methyl-2-propanol and optically active N-formylphenylalanine; the diastereomeric salt of optically active 1-amino-1-(2-methoxy-1-naphthyl)-2-methyl-2-propanol and optically active N-formylphenylalanine; the diastereomeric salt of optically active 1-amino-1-(2-ethoxy-1-naphthyl)-2-methyl-2-propanol and optically active N-formylphenylalanine; the diastereomeric salt of optically active 1-amino-1-(4-methoxy-1-naphthyl)-2-methyl-2-propanol and optically active N-formylphenylalanine; the diastereomeric salt of optically active 1-amino-1-(2,4-dimethoxy-1-naphthyl)-2-methyl-2-propanol and optically active N-formylphenylalanine; the diastereomeric salt of optically active 1-amino-1-(2-naphthyl)-2-methyl-2-propanol and optically active N-formylphenylalanine; the diastereomeric salt of optically active 1-amino-1-(7-methyl-2-naphthyl)-2-methyl-2-propanol and optically active N-formylphenylalanine; the diastereomeric salt of optically active 1-amino-1-(1-n-propyl-2-naphthyl)-2-methyl-2-propanol and optically active N-formylphenylalanine; the diastereomeric salt of optically active 1-amino-1-(6-methoxy-2-naphthyl)-2-methyl-2-propanol and optically active N-formylphenylalanine; the diastereomeric salt of optically active 1-amino-1-(3,8-dimethoxy-2-naphthyl)-2-methyl-2-propanol and optically active N-formylphenylalanine; and these diastereomeric salts in which the 2-methyl-2-propanol moieties are replaced with 2-ethyl-2-butanol, 2-n-propyl-2-pentanol, 2-n-butyl-2-hexanol, 2-isobutyl-4-methyl-2-pentanol, 2-n-pentyl-2-heptanol, 2-benzyl-3-phenyl-2-propanol, 2-(3-methylbenzyl)-3-(3-methylphenyl)-2-propanol, 2-(2-methylbenzyl)-3-(2-methylphenyl)-2-propanol, 2-(4-methylbenzyl)-3-(4-methylphenyl)-2-propanol, 2-(2-methoxybenzyl)-3-(2-methoxyphenyl)-2-propanol, 2-(3-methoxybenzyl)-3-(3-methoxyphenyl)-2-propanol, 2-(4-methoxybenzyl)-3-(4-methoxyphenyl)-2-propanol, 2-(1-naphthylmethyl)-3-(1-naphtyl)-2-propanol, and 2-(2-naphthylmethyl)-3-(2-naphtyl)-2-propanol.

Examples thereof also include the diastereomeric salt of optically active 2-amino-2-(1-naphthyl)-1,1-diphenylethanol and optically active N-formylphenylalanine; the diastereomeric salt of optically active 2-amino-2-(1-naphthyl)-1,1-di(3-methylphenyl)ethanol and optically active N-formylphenylalanine; the diastereomeric salt of optically active 2-amino-2-(l-naphthyl)-1,1-di(4-methylphenyl)ethanol and optically active N-formylphenylalanine; the diastereomeric salt of optically active 2-amino-2-(1-naphthyl)-1,1-di(2-methoxyphenyl)ethanol and optically active N-formylphenylalanine; the diastereomeric salt of optically active 2-amino-2-(1-naphthyl)-1,1-di(3-methoxyphenyl)ethanol and optically active N-formylphenylalanine; the diastereomeric salt of optically active 2-amino-2-(1-naphthyl)-1,1-di(4-methoxyphenyl)ethanol and optically active N-formylphenylalanine; the diastereomeric salt of optically active 1-[(amino)-(1-naphthyl)methyl]cyclopropanol and optically active N-formylphenylalanine; the diastereomeric salt of optically active 1-[(amino)-(1-naphthyl)methyl]cyclopentanol and optically active N-formylphenylalanine; and the diastereomeric salt of optically active 1-[(amino)-(1-naphthyl)methyl]cycloheptanol and optically active N-formylphenylalanine; and these compounds in which the 1-naphthyl group bonded to the carbon atom, to which the amino group of the optically active naphthyl alcohols composing the above exemplified respective diastereomeric salts is bonded, is replaced with a 4-fluoro-1-naphthyl, 2-methyl-1-naphthyl, 4-methyl-1-naphthyl, 2-methoxy-1-naphthyl, 2-ethoxy-1-naphthyl, 4-methoxy-1-naphthyl, 2,4-dimethoxy-1-naphthyl, 2-naphthyl, 7-methyl-2-naphthyl, 1-n-propyl-2-naphthyl, 6-methoxy-2-naphthyl, and 3,8-dimethoxy-2-naphthyl group.

The diastereomeric salt thus obtained can easily be converted into the optically active amino alcohol (30) as such or after purification by washing, recrystallization etc., followed by alkali treatment.

The alkali treatment can be carried out usually by mixing the diastereomeric salt and an alkali and the mixing temperature is usually in a range of 0 to 100° C. Examples of the alkali to be used include alkali metal hydroxides such as potassium hydroxide and sodium hydroxide and, usually, an aqueous solution thereof is used. When an aqueous alkali solution is used, the concentration of the alkali is usually 1 to 50% by weight, preferably 3 to 20% by weight. The amount of the alkali to be used is usually about 1 to 5 moles relative to 1 mole of the diastereomeric salt.

When the diastereomeric salt is subjected to the alkali treatment, usually, the optically active amino alcohol (30) is separated as an oil layer or precipitated in the form of solids from the alkali-treated mass and the optically active amino alcohol (30) can be isolated as such, or the optically active-amino alcohol (30) can be isolated by adding a water-insoluble organic solvent to the alkali-treated mass for extraction and distilling away the organic solvent from the organic layer obtained. Examples of the water-insoluble organic solvent include ether solvents such as diethyl ether and methyl tert-butyl ether; ester solvents such as ethyl acetate; aromatic hydrocarbon solvents such as toluene, xylene, and chlorobenzene; halogenated hydrocarbon solvents such as dichloromethane and chloroform, and the amount thereof to be used is usually in a range of 0.5 to 50 parts by weight relative to 1 part by weight of the diastereomeric salt used. The water-insoluble organic solvent can be added previously at the time of alkali treatment of the diastereomeric salt.

The optically active amino alcohol (30) can also be isolated by previously treating the diastereomeric salt with an acid and then subjecting to the alkali treatment. When the diastereomeric salt is previously treated with an acid, the optically active N-formylphenylalanine is released. Then, preferably, the alkali treatment is carried out after separating the optically active N-formylphenylalanine released.

The acid treatment is usually carried out by mixing the diastereomeric salt and an aqueous solution of an acid, and the mixing temperature is usually 0 to 100° C. As the acid to be used, usually, there are an aqueous solution of a mineral acid such as hydrochloric acid, sulfuric acid, and phosphoric acid and the concentration is usually 1 to 50% by weight, preferably 5 to 40% by weight. The amount of the acid to be used is usually 1 to 5 moles, preferably 1 to 2 moles relative to 1 mole of the diastereomeric salt.

As the separation method of the optically active N-formylphenylalanine released, there is, for example, a method for extracting it by adding a water-insoluble organic solvent to the mass in which the diastereomeric salt is previously subjected to the acid treatment. As the water-insoluble organic solvent, there are, for example, the same solvents as described above, and the amount thereof to be used is usually 0.5 to 20 part by weight to 1 part by weight of the diastereomeric salt used. The water-insoluble organic solvent causes no problem even when it is previously added at the time of acid treatment of the diastereomeric salt.

When a part or all of the released optically active N-formylphenylalanine is precipitated in the acid-treated mass, the mass can also be filtered as such or, if necessary, after further cooling, to separate the released optically active N-formylphenylalanine.

In the alkali treatment to be carried out successively to the acid treatment, an aqueous solution of an alkali metal hydroxide such as potassium hydroxide and sodium hydroxide is used and the concentration of the solution is usually 1 to 50% by weight, preferably 5 to 20% by weight. The alkali is used in such an amount that pH of the mass to be treated becomes 10 or higher, and the treatment temperature is usually 0 to 100° C.

When the alkali treatment of the diastereomeric salt is carried out after the previous acid treatment, the optically active amino alcohol (30) is usually separated as an oil layer or precipitated in the form of solids in the alkali-treated mass, and the oil layer or the solids can be isolated as such. Alternatively, the optically active amino alcohol (30) can be isolated by adding a water-insoluble organic solvent to the alkali-treated mass for extraction and distilling away the organic solvent from the organic layer obtained. As the water-insoluble organic solvent, there are, for example, the same solvents as described, and the amount thereof to be used is usually 0.5 to 50 parts by weight relative to 1 part by weight of the diastereomer salt used in the treatment. The water-insoluble organic solvent can previously be added at the time of the alkali treatment.

The optically active N-formylphenylalanine used can easily be recovered and the recovered optically active N-formylphenylalanine can be reused for the reaction of the amino alcohol (40) and the optically active N-formylphenylalanine. When the diastereomeric salt is alkali-treated without being previously treated with an acid, the optically active N-formylphenylalanine can be recovered by acid treatment of the treated mass obtained after recovering the optically active amino alcohol (30). When the diastereomeric salt is alkali-treated after previous treatment with an acid, a part or all of the optically active N-formylphenylalanine is usually precipitated in the acid-treated mass obtained by the acid treatment and the mass is filtered as such or, if necessary, after further cooled to recover the optically active N-formylphenylalanine. Alternatively, a water-insoluble organic solvent is added to the acid-treated mass for extraction and the organic solvent is distilled away from the organic layer obtained to recovery the optically active N-formylphenylalanine. As the water-insoluble organic solvent, there are, for example, the same solvents as described above. The water-insoluble organic solvent can be added previously at the time of acid treatment.

The amino alcohol (40) can be produced by the method involving the following steps (A) to (D).

That is, (A) reacting a naphthylglycine compound represented by the formula (41):

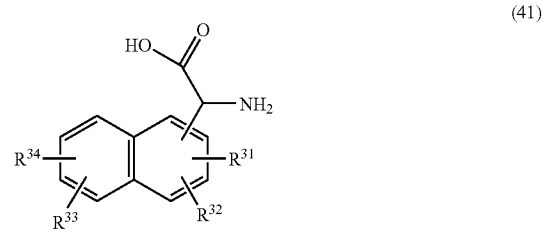

(41)

wherein $R^{31}$, $R^{32}$, $R^{33}$, and $R^{34}$ are as defined above (hereinafter, simply referred to as the naphthylglycine compound (41)), with a chlorinating agent and an alcohol represented by the formula (42):

$R^9OH$ (42)

wherein $R^9$ represents a $C_{1-6}$ alkyl group (hereinafter, simply referred to as the alcohol (42)), to obtain an amino acid ester hydrochloride represented by the formula (43):

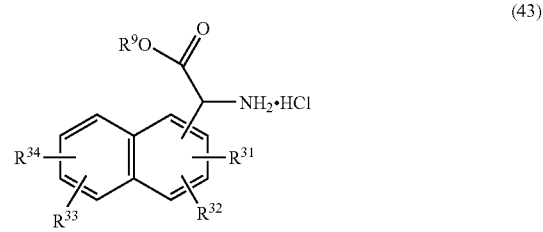

(43)

wherein $R^{31}$, $R^{32}$, $R^{33}$, $R^{34}$ and $R^9$ are as described above (hereinafter, simply referred to as the amino acid ester hydrochloride (43)), (B) reacting the amino acid ester hydrochloride (43) obtained in the above step (A) with a compound represented by the formula (44):

$(C_nF_{2n+1}CO)_2O$ (44)

wherein n represents 1, 2 or 3 (hereinafter, simply referred to as the compound (44)), or the formula (45):

$C_nF_{2n+1}COX$ (45)

wherein n is as described above; and X represents a chlorine atom, a bromine atom, or an iodine atom (hereinafter, simply referred to as the compound (45)), in the presence of a tertiary amine to obtain a compound represented by the formula (46):

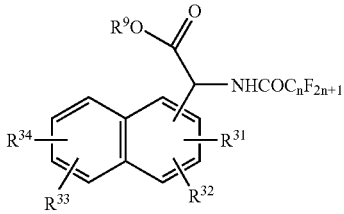

(46)

wherein $R^{31}$, $R^{32}$, $R^{33}$, $R^{34}$, $R^9$ and n are as described above (hereinafter, simply referred to as the compound (46)), (C) reacting the compound (46) obtained in the above step (B) with a compound represented by the formula (47):

$$R^{35}MgX' \quad (47)$$

wherein $R^{35}$ represents a $C_{1-6}$ alkyl group, a substituted or unsubstituted aralkyl group, or a substituted or unsubstituted phenyl group; and X' represents a halogen atom (hereinafter, simply referred to as the compound (47)), or a compound represented by the formula (48):

$$X'—Mg—R^{35'}—Mg—X \quad (48)$$

wherein $R^{35'}$ represents a $C_{2-6}$ alkylene group and X' is as defined above (hereinafter, simply referred to as the compound (48)) to obtain a compound represented by the formula (49):

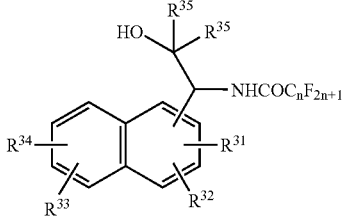

(49)

wherein $R^{31}$, $R^{32}$, $R^{33}$, $R^{34}$, $R^{35}$ and n are as defined above (hereinafter, simply referred to as the compound (49)), and (D) reacting the compound (49) obtained in the above step (C) with a base to obtain the naphthyl alcohol (40).

First, the step (A) will be illustrated. The step (A) is that for obtaining the amino acid ester hydrochloride (5) by reaction of the naphthylglycine compound (41) and a chlorinating agent in the presence of the alcohol (42).

Examples of the naphthylglycine compound (3) include 1-naphthylglycine, 2-methyl-1-naphthylglycine, 4-methyl-1-naphthylglycine, 2-methoxy-1-naphthylglycine, 2-ethoxy-1-naphthylglycine, 4-methoxy-1-naphthylglycine, 2,4-dimethoxy-1-naphthylglycine, 2-naphthylglycine, 7-methyl-2-naphthylglycine, 1-n-propyl-2-naphthylglycine, 6-methoxy-2-naphthylglycine, and 3,8-dimethoxy-2-naphthylglycine.

The naphthylglycine compound (3) may be commercially available one or may be produced by reacting a naphthylaldehyde with a cyano compound such as sodium cyanide, and ammonium carbonate, followed by treating the reaction product with an alkali such as potassium hydroxide (e.g. Experimental Chemistry, 4th edition, vol. 22, p. 195, Chemical Society of Japan).

Examples of the chlorinating agent include thionyl chloride and carbonyl chloride, and the amount to be used is usually 1 mole or more, preferably 1.1 moles or more relative to 1 mole of the naphthylglycine compound (41). There is no specific upper limit, when it is too much, it may results in economical disadvantage. Therefore, it is practically 2-fold mole or less.

In the formula of the alcohol (42), $R^6$ represents a $C_{1-6}$ alkyl group and examples thereof include the same groups as described above. Examples of the alcohol (42) include methanol, ethanol, n-propanol, isopropanol, n-butanol, isobutanol, sec-butanol, pentanol, and hexanol.

The amount of the alcohol (42) to be used is usually 1 mole or more relative to 1 mole of the naphthylglycine compound (41) and there is no specific upper limit. The alcohol may be used in large excess to also serve as a solvent.

Usually, the reaction of the naphthylglycine compound (41), the chlorinating agent, and the alcohol (42) is carried out by mixing these three reactants and the mixing order is not particularly limited. Further, the reaction is usually carried out in a solvent and examples of the solvent include aliphatic hydrocarbon solvents such as hexane and heptane; aromatic hydrocarbon solvents such as toluene, xylene, and chlorobenzene; halogenated hydrocarbon solvents such as dichloromethane and chloroform; ether solvents such as diethyl ether, methyl tert-butyl ether, tetrahydrofuran, dioxane, and dimethoxyethane; ester solvents such as ethyl acetate; and nitrile solvents such as acetonitrile. They may be used alone or in the form of a mixed solvent. Also, as described above, the alcohol (42) may be used as the solvent. The amount of the solvent to be used may be that suitable for permitting to stir the reaction mass. Usually, it is 1 part by weight or more relative to 1 part by weight of the naphthylglycine compound (41) and there is no specific upper limit.

The reaction temperature is usually 0° C. to a refluxing temperature of the reaction mixture, preferably 10 to 60° C.

After completion of the reaction, the reaction mixture is subjected to concentration treatment or precipitation treatment to isolate the amino acid ester hydrochloride (43). Sometimes, a part or all of the formed amino acid ester hydrochloride (43) is precipitated in the reaction mixture and in such a case, the reaction mixture as such or, after partially concentrating and, if necessary, cooling, is filtrated to isolate the amino acid ester hydrochloride (43). Although the isolated amino acid ester hydrochloride (43) as such can be used in the next step (B), preferably, after washing with a solvent which can scarcely dissolve the amino acid ester hydrochloride (43) such as the above ether solvent, because, sometimes, it contains the unreacted alcohol (42) or chlorinating agent.

Examples of the amino acid ester hydrochloride (43) thus obtained include 1-naphthylglycine methyl ester hydrochloride, 2-methyl-1-naphthylglycine methyl ester hydrochloride, 4-methyl-1-naphthylglycine methyl ester hydrochloride, 2-methoxy-1-naphthylglycine methyl ester hydrochloride, 2-ethoxy-1-naphthylglycine methyl ester hydrochloride, 4-methoxy-1-naphthylglycine methyl ester hydrochloride, 2,4-dimethoxy-1-naphthylglycine methyl ester hydrochloride, 2-naphthylglycine methyl ester hydrochloride, 7-methyl-2-naphthylglycine methyl ester hydrochloride, 1-n-propyl-2-naphthylglycine methyl ester hydrochloride, 6-methoxy-2-naphthylglycine methyl ester hydrochloride, 3,8-dimethoxy-2-naphthylglycine methyl ester hydrochloride, and compounds wherein these respective methyl esters are replaced with ethyl esters, n-propyl esters, isopropyl esters, n-butyl esters, isobutyl esters, and sec-butyl esters.

Then, the step (B) will be illustrated. The step (B) is that for obtaining the compound (46) by reaction of the amino acid ester hydrochloride (43) obtained in the above step (A) and either the compound (44) or the compound (45) in the presence of the tertiary amine.

In the formula of the compound (44), n represents 1, 2, or 3. Examples of the compound (6) include trifluoroacetic anhydride, 2,2,3,3,3-pentafluoropropionic anhydride, 2,2,3,3,4,4,4-heptafluorobutanoic anhydride. In the formula of the compound (45), X represents a chlorine, bromine, or iodine atom and examples of the compound (45) include trifluoroacetic acid chloride, 2,2,3,3,3-pentafluoropropionic acid chloride, and 2,2,3,3,4,4,4-heptafluorobutanoic acid chloride. As the compounds (44) and (45), for example, commercially available compounds can be used.

The amount of the compound (44) or the compound (45) to be used is usually 0.8 to 2 moles, preferably 1 to 1.5 moles relative to 1 mole of the amino acid ester hydrochloride (43).

Examples of the tertiary amine include triethylamine, tri-n-propylamine, tri-n-butylamine, diisopropylethyamine, N,N-dimethylaniline, N,N-diethylaniline, pyridine, and 4-(N,N-dimethylamino)pyridine. The amount thereof to be used is usually 1.5 to 3 moles, preferably 1.8 to 2.5 moles relative to 1 mole of the amino acid ester hydrochloride (43).

Usually, the reaction of the amino acid ester hydrochloride (43) and either the compound (44) or the compound (45) is carried out by mixing both reactants and the mixing order is not particularly limited. The reaction is usually carried out in a solvent and examples of the solvent include the above-mentioned aliphatic hydrocarbon solvents, aromatic hydrocarbon solvents, halogenated hydrocarbon solvents, ether solvents, ester solvents, and nitrile solvents. They may be used alone or in the form of a mixed solvent. The amount thereof to be used may be that suitable for permitting to stir the reaction mixture. Usually, it is 1 part by weight or more relative to 1 part by weight of the amino acid ester hydrochloride (43).

The reaction temperature is usually 0° C. or lower, preferably −20 to −50° C.

After completion of the reaction, the reaction mixture is mixed with water and, if necessary, a water-insoluble organic solvent is added, and extracting treatment is conducted, and the organic layer obtained is concentrated to isolate the compound (46). The isolated compound (46) as such, or after further purifying by a conventional purification means such as recrystallization or column chromatography, can be used in the next step (C).

Examples of the compound (46) include N-(trifluoroacetyl)-1-naphthylglycine methyl ester, N-(trifluoroacetyl)-2-methyl-1-naphthylglycine methyl ester, N-(trifluoroacetyl)-4-methyl-1-naphthylglycine methyl ester, N-(trifluoroacetyl)-2-methoxy-1-naphthylglycine methyl ester, N-(trifluoroacetyl)-2-ethoxy-1-naphthylglycine methyl ester, N-(trifluoroacetyl)-4-methoxy-1-naphthylglycine methyl ester, N-(trifluoroacetyl)-2,4-dimethoxy-1-naphthylglycine methyl ester, N-(trifluoroacetyl)-2-naphthylglycine methyl ester, N-(trifluoroacetyl)-7-methyl-2-naphthylglycine methyl ester, N-(trifluoroacetyl)-1-n-propyl-2-naphthylglycine methyl ester, N-(trifluoroacetyl)-6-methoxy-2-naphthylglycine methyl ester, N-(trifluoroacetyl)-3,8-dimethoxy-2-naphthylglycine methyl ester; compounds wherein the above-exemplified respective methyl esters are replaced with ethyl esters, n-propyl esters, isopropyl esters, n-butyl esters, isobutyl esters, and sec-butyl esters; and compounds wherein the trifluoroacetyl group, the substituent on the amino group of the above-exemplified compounds, is replaced with 2,2,3,3,3-pentafluoropropionyl and 2,2,3,3,4,4,4-heptafluorobutyryl group.

Then, the step (C) will be illustrated. The step (C) is that for obtaining the compound (49) by reaction of the compound (46) obtained in the above step (B) and either the compound (47) or the compound (48).

In the formula of the compound (48), $R^{35'}$ represents $C_{2-6}$ alkylene and examples thereof include an ethylene, trimethylene, tetramethylene, pentamethylene, and hexamethylene group.

Examples of the compound (47) or the compound (48) include methylmagnesium chloride (or bromide), ethylmagnesium chloride (or bromide), n-propylmagnesium chloride (or bromide), n-butylmagnesium chloride (or bromide), isobutylmagnesium chloride (or bromide), n-pentylmagnesium chloride (or bromide), n-hexylmagnesium chloride (or bromide), benzylmagnesium chloride (or bromide), 2-methylbenzylmagnesium chloride (or bromide), 4-methylbenzylmagnesium chloride (or bromide), 2-methoxybenzylmagnesium chloride (or bromide), 3-methoxybenzylmagnesium chloride (or bromide), 4-methoxybenzylmagnesium chloride (or bromide), 1-naphthylmethylmagnesium chloride (or bromide), 2-naphthylmethylmagnesium chloride (or bromide), phenylmagnesium chloride (or bromide), 3-methylphenylmagnesium chloride (or bromide), 4-methylphenylmagnesium chloride (or bromide), 2-methoxyphenylmagnesium chloride (or bromide), 3-methoxyphenylmagnesium chloride (or bromide), 4-methoxyphenylmagnesium chloride (or bromide), ethylenedimagnesium chloride (or bromide), tetramethylenedimagnesium chloride (or bromide), and hexamethylenedimagnesium chloride (or bromide). As the compound (47) or the compound (48), commercially available compounds can be used or they can be produced by reaction of the corresponding halogen compounds and metal magnesium.

The amount to be used, in the case of using the compound (47), is usually 2 to 3 moles, preferably 2.1 to 2.7 moles relative to 1 mole of the compound (46). The amount to be used, in the case of using the compound (48), is usually 1 to 1.5 moles, preferably 1.1 to 1.4 moles relative to 1 mole of the compound (46).

Usually, the reaction of the compound (46) and either the compound (47) or the compound (48) is carried out by mixing both reactants in a solvent and the mixing order is not particularly limited. Examples of the solvent include the above-mentioned ether solvents such as diethyl ether and the amount thereof to be used is usually 1 to 50 parts by weight, preferably 3 to 20 parts by weight relative to 1 part by weight of the compound (46). If necessary, the above-mentioned aromatic hydrocarbon solvents such as toluene may be mixed thereto.

The reaction temperature is usually −20° C. to a refluxing temperature of the reaction mixture, preferably −10 to 30° C.

After completion of the reaction, the reaction mixture and an aqueous solution of a mineral acid such as hydrochloric acid, sulfuric acid, or phosphoric acid are mixed for extraction treatment and the organic layer obtained is concentrated to isolate the compound (49). The isolated compound (49) as such or, after further purifying by a conventional purification means such as recrystallization or column chromatography, can be used in the next step (D).

Examples of the compound (49) thus obtained include 1-(trifluoroacetylamino)-(1-naphthyl)-2-methyl-2-propanol, 1-(trifluoroacetylamino)-1-(4-fluoro-1-naphthyl)-2-methyl-2-propanol, 1-(trifluoroacetylamino)-1-(2-methyl-1-naphthyl)-2-methyl-2-propanol, 1-(trifluoroacetylamino)-1-(4-methyl-1-naphthyl)-2-methyl-2-propanol, 1-(trifluoroacetylamino)-1-(2-methoxy-1-naphthyl)-2-methyl-2-propanol, 1-(trifluoroacetylamino)-1-(2-ethoxy-1-naphthyl)-2-methyl-2-propanol, 1-(trifluoroacetylamino)-1-(4-methoxy-1-naphthyl)-2-methyl-2-propanol, 1-(trifluoroacetylamino)-1-(2,4-dimethoxy-1-naphthyl)-2-methyl-2-propanol, 1-(trifluoroacetylamino)-1-(2-naphthyl)-2-methyl-2-propanol, 1-(trifluoroacetylamino)-1-(7-methyl-2-naphthyl)-2-methyl-2-propanol, 1-(trifluoroacetylamino)-1-(1-n-propyl-2-naphthyl)-2-methyl-2-propanol, 1-(trifluoroacetylamino)-1-(6-methoxy-2-naphthyl)-2-methyl-2-propanol, 1-(trifluoroacetylamino)-1-(3,8-dimethoxy-2-naphthyl)-2-methyl-2-propanol; compounds wherein the 2-methyl-2-propanol moieties of the above exemplified compounds are replaced with 2-ethyl-2-butanol, 2-n-propyl-2-pentanol, 2-n-butyl-2-hexanol, 2-isobutyl-4-methyl-2-pentanol, 2-n-pentyl-2-heptanol, 2-benzyl-3-phenyl-2-propanol, 2-(3-methylbenzyl)-3-(3-methylphenyl)-2-propanol, 2-(2-methylbenzyl)-3-(2-methylphenyl)-2-propanol, 2-(4-methylbenzyl)-3-(4-methylphenyl)-2-propanol, 2-(2-methoxybenzyl)-3-(2-methoxyphenyl)-2-propanol, 2-(3-methoxybenzyl)-3-(3-methoxyphenyl)-2-propanol, 2-(4-methoxybenzyl)-3-(4-methoxyphenyl)-2-propanol, 2-(1-naphthylmethyl)-3-(1-naphthyl)-2-propanol, 2-(2-naphthylmethyl)-3-(2-naphthyl)-2-propanol; and compounds wherein the trifluoroacetylamino group of the above exemplified compounds are replaced with 2,2,3,3,3-pentafluoropropionylamino and 2,2,3,3,4,4,4-heptafluorobutyrylamino.

Further, examples thereof also include 2-(trifluoroacetylamino)-2-(1-naphthyl)-1,1-diphenylethanol, 2-(trifluoroacetylamino)-2-(1-naphthyl)-1,1-di(3-methylphenyl)ethanol, 2-(trifluoroacetylamino)-2-(1-naphthyl)-1,1-di(4-methylphenyl)ethanol, 2-(trifluoroacetylamino)-2-(1-naphthyl)-1,1-di(2-methoxyphenyl)ethanol, 2-(trifluoroacetylamino)-2-(1-naphthyl)-1,1-di(3-methoxyphenyl)ethanol, 2-(trifluoroacetylamino)-2-(1-naphthyl)-1,1-di(4-methoxyphenyl)ethanol, 1-[(trifluoroacetylamino)-(1-naphthyl)methyl]cyclopropanol, 1-[(trifluoroacetylamino)-(1-naphthyl)methyl]cyclopentanol, 1-[(trifluoroacetylamino)-(1-naphthyl)methyl]cycloheptanol, and compounds wherein the 1-naphthyl group bonded to the carbon atom, to which the trifluoroacetylamino group of the above exemplified compounds is bonded, is replaced with a 4-fluoro-1-naphthyl, 2-methyl-1-naphthyl, 4-methyl-1-naphthyl, 2-methoxy-1-naphthyl, 2-ethoxy-1-naphthyl, 4-methoxy-1-naphthyl, 2,4-dimethoxy-1-naphthyl, 2-naphthyl, 7-methyl-2-naphthyl, 1-n-propyl-2-naphthyl, 6-methoxy-2-naphthyl, and 3,8-dimethoxy-2-naphthyl group.

Finally, the step for obtaining the amino alcohol (40) by reacting the compound (49) obtained in the above step (C) with a base will be illustrated.

Examples of the base include alkali metal hydroxides such as sodium hydroxide and potassium hydroxide and alkaline earth metal hydroxides such as calcium hydroxide and barium hydroxide and, usually, aqueous solutions thereof are used. The amount of the base to be used is usually 1 to 3 moles, preferably 1.2 to 2.5 moles relative to 1 mole of the compound (49). Usually, the reaction of the compound (49) and the base is carried out in a solvent and examples of the solvent include the above-mentioned alcohol solvents, water, and mixed solvents of water and the alcohol solvents. The amount thereof to be used is usually 2 to 30 parts by weight, preferably 3 to 15 parts by weight relative to 1 part by weight of the compound (49).

The reaction temperature is usually 0° C. to a refluxing temperature of the reaction mixture, preferably 10 to 60° C.

After completion of the reaction, for example, the reaction mixture is concentrated, and then mixed with a water-insoluble organic solvent for extraction treatment and the organic layer obtained is concentrated to isolate the amino alcohol (40). Examples of the water-insoluble organic solvent include the same solvents as those described above. The isolated amino alcohol (40) can be further purified by a conventional purification means such as recrystallization or column chromatography.

INDUSTRIAL APPLICABILITY

By using the asymmetric copper complex produced from the novel optically active bisoxazoline compound of the present invention and the copper compound, it is possible to produce an optically active cyclopropane compound with good diastereoselectivity and enantioselectivity at a high yield and thus the present invention is more advantageous from the industrial viewpoint.

EXAMPLES

The present invention will be further illustrated in more detail by Examples. The present invention is not limited to these Examples.

Example 1

Under a nitrogen atmosphere, 1.2 g of (S)-1-amino-1-(1-naphthyl)-2-methyl-2-propanol, 0.37 g of dimethyl malonate, and 70 mL of xylene were reacted by mixing and stirring at an inner temperature of 130° C. for 5 hours to obtain a reaction mixture containing N,N'-bis[(1S)-(1-naphthyl)-2-hydroxy-2-methylpropyl]propane-1,3-diamide. 79 mg of titanium tetraisopropoxide was added to the reaction mixture and the mixture was stirred at an inner temperature of 130° C. for 48 hours to effect reaction. After completion of the reaction, the reaction mixture was concentrated and the concentrated residue was purified by column chromatography (neutral alumina, chloroform) to obtain 0.7 g of a white powder of bis[2-[(4S)-(1-naphthyl)-5,5-dimethyloxazoline]]methane (yield: 54%).

$^1$H-NMR data of bis[2-[(4S)-(1-naphthyl)-5,5-dimethyloxazoline]]methane (δ: ppm, CDCl$_3$ solvent, TMS standard) 0.84 (s, 6H), 1.82 (s, 6H), 3.69 (s, 2H), 5.81 (s, 2H), 7.43-7.59 (m, 8H), 7.75-7.95 (m, 6H).

Example 2

According to the same manner as that described in Example 1, 0.79 g of a pale yellow powder of bis[2-[(4S)-(2-naphthyl)-5,5-dimethyloxazoline]]methane (yield: 61%) was obtained except that 1.2 g of (S)-1-amino-1-(2-naphthyl)-2-methyl-2-propanol was used in place of 1.2 g of (S)-1-amino-1-(1-naphthyl)-2-methyl-2-propanol.

$^1$H-NMR data of bis[2-[(4S)-(2-naphthyl)-5,5-dimethyloxazoline]]methane (δ: ppm, CDCl$_3$ solvent, TMS standard) 0.92 (s, 6H), 1.69 (s, 6H), 3.63 (s, 2H), 5.10 (s, 2H), 7.40-7.48 (m, 6H), 7.70-7.83 (m, 8H).

Example 3

Under a nitrogen atmosphere, 2 g of (S)-1-amino-1-(1-naphthyl)-2-methyl-2-propanol, 1.1 g of triethylamine (dehydrated), and 17 mL of dichloromethane (dehydrated) were mixed and then cooled to an inner temperature of −10° C. 0.8 g of dimethylmalonic acid dichloride was added dropwise thereto over 3 minutes and the resulting mixture was warmed to room temperature. The mixture was stirred as such for 6 hours to effect reaction. After completion of the reaction, 20 mL of an aqueous saturated ammonium chloride solution was added thereto to separate into layers. The organic layer obtained was washed three times with 25 mL of water and concentrated. The concentrated residue was dried. under reduced pressure at an inner temperature of 40° C. to obtain 2.5 g of N,N'-bis[(1S)-(1-naphthyl)-2-hydroxy-2-methylpropyl]-2,2-dimethylpropane-1,3-diamide (yield: 100%).

$^1$H-NMR data of N,N'-bis[(1S)-(1-naphthyl)-2-hydroxy-2-methylpropyl]-2,2-dimethylpropane-1,3-diamide (δ: ppm, CD$_3$OD solvent, TMS standard) 0.90 (s, 6H), 1.36 (s, 6H), 1.46 (s, 6H), 4.85 (s, 4H), 5.47 (s, 2H), 7.13 (t, J=9.0 Hz, 2H), 7.33-7.35 (m, 2H), 7.45-7.52 (m, 4H), 7.70 (d, J=9.0 Hz, 2H), 7.83-7.86 (m, 2H), 8.29 (d, J=9.0 Hz, 2H).

1.8 g of the N,N'-bis[(1S)-(1-naphthyl)-2-hydroxy-2-methylpropyl]-2,2-dimethylpropane-1,3-diamide thus obtained and 90 mL of xylene were mixed and stirred at an inner temperature of 130° C. for 1 hour. Then, 97 mg of titanium tetraisopropoxide was added to the mixture, and the mixture was stirred at the same temperature for 48 hours to effect reaction. After completion of the reaction, the reaction mixture was concentrated and the concentrated residue was purified by column chromatography (neutral alumina, hexane/ethyl acetate=10/1 (by volume)) to obtain 1.4 g of a white powder of 2,2-bis[2-[(4S)-(1-naphthyl)-5,5-dimethyloxazoline)]]propane (yield: 83%).

$^1$H-NMR data of 2,2-bis[2-[(4S)-(1-naphthyl)-5,5-dimethyloxazoline]]propane (δ: ppm, CDCl$_3$ solvent, TMS standard) 0.81 (s, 6H), 1.78 (s, 6H), 1.81 (s, 6H), 5.85 (s, 2H), 7.39-7.55 (m, 8H), 7.75 (d, J=9.0 Hz, 2H), 7.87 (d, J=9.0 Hz, 2H), 7.94 (d, J=9.0 Hz, 2H).

Example 4

Under a nitrogen atmosphere, 1.5 g of (S)-1-amino-1-(2-naphthyl)-2-methyl-2-propanol, 0.84 g of triethylamine (dehydrated), and 13 mL of dichloromethane (dehydrated) were mixed and then cooled to an inner temperature of −10° C. 0.6 g of dimethylmalonic acid dichloride was added dropwise thereto over 3 minutes. The resulting mixture was warmed to room temperature. The mixture was stirred as such for 7 hours to effect reaction. After completion of the reaction, 20 mL of an aqueous saturated ammonium chloride solution was added thereto to separate into layers. The organic layer obtained was washed three times with 25 mL of water and concentrated. The concentrated residue was dried under reduced pressure at an inner temperature of 40° C. to obtain 1.8 g of N,N'-bis[(1S)-(2-naphthyl)-2-hydroxy-2-methylpropyl]-2,2-dimethylpropane-1,3-diamide (yield: 100%).

$^1$H-NMR data of N,N'-bis[(1S)-(2-naphthyl)-2-hydroxy-2-methylpropyl]-2,2-dimethylpropane-1,3-diamide (δ: ppm, CD$_3$OD solvent, TMS standard) 1.00 (s, 6H), 1.30 (s, 6H), 1.50 (s, 6H), 4.86 (s, 4H), 4.87 (s, 2H), 7.27-7.45 (m, 8H), 7.66-8.06 (m, 6H).

1.8 g of the N,N'-bis[(1S)-(2-naphthyl)-2-hydroxy-2-methylpropyl]-2,2-dimethylpropane-1,3-diamide thus obtained and 90 mL of xylene were mixed and stirred at an inner temperature of 130° C. for 1 hour. Then, 97 mg of titanium tetraisopropoxide was added to the reaction mixture and the mixture was stirred at the same temperature for 48 hours to effect reaction. After completion of the reaction, the reaction mixture was concentrated and the concentrated residue was purified by column chromatography (neutral alumina, hexane/ethyl acetate=5/1 (by volume)) to obtain 1.3 g of a white powder of 2,2-bis[2-[(4S)-(2-naphthyl)-5,5-dimethyloxazoline]]propane (yield: 77%).

$^1$H-NMR data of 2,2-bis[2-[(4S)-(2-naphthyl)-5,5-dimethyloxazoline]]propane (δ: ppm, CDCl$_3$ solvent, TMS standard) 0.90 (s, 6H), 1.66 (s, 6H), 1.76 (s, 6H), 5.05 (s, 2H), 7.34-7.46 (m, 6H), 7.66-8.05 (m, 8H).

Example 5

Under a nitrogen atmosphere, 1.5 g of (S)-1-amino-1-(1-naphthyl)-2-methyl-2-propanol, 0.84 g of triethylamine (dehydrated), and 13 mL of dichloromethane (dehydrated)were mixed and then cooled to an inner temperature −10° C. Then, 0.58 g of 1,1-cyclopropanedicarboxylic acid dichloride was added dropwise thereto over 3 minutes and the resulting mixture was warmed to room temperature. The mixture was stirred for 7 hours as such to effect reaction. After completion of the reaction, 20 mL of an aqueous saturated ammonium chloride solution was added thereto to separate into layers. The organic layer obtained was washed three times with 25 mL of water and concentrated. The concentrated residue was dried under reduced pressure at an inner temperature of 40° C. to obtain 1.9 g of N,N'-bis[(1S)-(1-naphthyl)-2-hydroxy-2-methylpropyl]cyclopropane-1,1-dicarboxamide (yield: 100%).

$^1$H-NMR data of N,N'-bis[(1S)-(1-naphthyl)-2-hydroxy-2-methylpropyl]cyclopropane-1,1-dicarboxamide (δ: ppm, CD$_3$OD solvent, TMS standard) 0.97 (s, 6H), 1.0-1.08 (m, 2H), 1.32-1.35 (m, 2H), 1.35 (s, 6H), 4.87 (s, 4H), 5.86 (s, 2H), 7.32-7.54 (m, 8H), 7.76 (d, J=9.0 Hz, 2H), 7.85 (d, J=9.0 Hz, 2H), 8.31 (d, J=9.0 Hz, 2H).

1.83 g of the N,N'-bis[(1S)-(1-naphthyl)-2-hydroxy-2-methylpropyl]cyclopropane-1,1-dicarboxamide thus obtained and 100 mL of xylene were mixed and stirred at an inner temperature of 130° C. for 1 hour and then 99 mg of titanium tetraisopropoxide was added to the reaction mixture. The mixture was stirred at the same temperature for 40 hours to effect reaction. After completion of the reaction, the reaction mixture was concentrated and the concentrated residue was purified by column chromatography (silica gel, hexane/ethyl acetate=4/1 (by volume)) to obtain 1.23 g of a pale yellow powder of 1,1-bis[2-[(4S)-(1-naphthyl)-5,5-dimethyloxazoline]]cyclopropane (yield: 72%).

$^1$H-NMR data of 1,1-bis[2-[(4S)-(1-naphthyl)-5,5-dimethyloxazoline]]cyclopropane (δ: ppm, CDCl$_3$ solvent, TMS standard) 0.83 (s, 6H), 1.53-1.61 (m, 2H), 1.69-1.75 (m, 2H), 1.77 (s, 6H), 5.76 (s, 2H), 7.46-7.54 (m, 8H), 7.78 (d, J=9.0 Hz, 2H), 7.86-7.94 (m, 4H).

Example 6

In a 50 mL Schlenk tube purged with nitrogen, 27 mg of 2,2-bis[2-[(4S)-(1-naphthyl)-5,5-dimethyloxazoline]]propane, obtained in Example 3, was added to a white suspension containing 18 mg of cuprous trifluoromethanesulfonate and 5 mL of dichloroethane , and the resulting mixture was stirred at room temperature for 10 minutes to prepare a blue colored homogeneous solution containing an asymmetric copper complex. Then, 7.8 g of 2,5-dimethyl-2,4-hexadiene was added thereto and the inner temperature was adjusted to 40° C. 1.1 g of ethyl diazoacetate was added dropwise thereto over 2 hours and the resulting mixture was stirred at the same temperature for 30 minutes to effect reaction. The reaction mixture was analyzed by gas chromatography to find the production of ethyl 2,2-dimethyl-3-(2-methyl-1-propenyl)cyclopropanecarboxylate at 93% yield (based on ethyl diazoacetate) and trans-isomer/cis-isomer ratio=69/31. Also, optical purity was analyzed by liquid chromatography to find the optical purity of the trans-isomer was 82% e.e. and that of the cis-isomer was 8% e.e. In this connection, the trans-isomer means the compound having the ester group at 1-position and 2-methyl-1-propenyl group at 3-position on the opposite side with respect to the cyclopropane ring plane and the cis-isomer means the compound having the ester group at 1-position and 2-methyl-1-propenyl group at 3-position on the same side (hereinafter, the same in the following Examples).

Example 7

According to the same manner as that described in Example 6, tert butyl 2,2-dimethyl-3-(2-methyl-1-propenyl) cyclopropanecarboxylate was obtained in a yield of 92% (based on tert-butyl diazoacetate) except that 1.4 g of tert-butyl diazoacetate was used in place of 1.1 g of ethyl diazoacetate. Trans-isomer/cis-isomer ratio was 87/13. The reaction mixture was concentrated and a 1 g portion of the resulting concentrated residue was taken out. 0.1 mL of trifluoroacetic acid and 5 mL of toluene were added thereto and the resulting mixture was stirred at an inner temperature of 100° C. for 3 hours to effect reaction, and 2,2-dimethyl-3-(2-methyl-1-propenyl)cyclopropanecarboxylic acid was obtained. The 2,2-dimethyl-3-(2-methyl-1-propenyl)cyclopropanecarboxylic acid obtained was reacted with 1-menthol and the produced 1-menthyl ester was analyzed by gas chromatography to find the optical purity of the trans-isomer was 95% e.e. and that of the cis-isomer was 69% e.e.

Experimental Example 1

In a 50 mL Schlenk tube purged with nitrogen, 22 mg of 2,2-bis[2-[(4S)-1-naphthyloxazoline]]propane was added to a white suspension containing 18 mg of cuprous trifluoromethanesulfonate and 5 mL of dichloroethane and stirred at a room temperature for 10 minutes to prepare a blue color homogeneous solution of an asymmetric copper complex. After that, 7.8 g of 2,5-dimethyl-2,4-hexadiene was added thereto and the inner temperature was adjusted to 40° C. and 1.4 g of tert-butyl diazoacetate was dropwise added for 2 hours and the resulting mixture was stirred at the same temperature further for 30 minutes to effect reaction and tert-butyl 2,2-dimethyl-3-(2-methyl-1-propenyl)cyclopropanecarboxylate was obtained in a yield of 89% (based on tert-butyl diazoacetate). Trans-isomer/cis-isomer ratio=81/19. The optical purity of the trans-isomer was 86% e.e. and that of the cis-isomer was 60% e.e.

Example 8

23.3 g of 1-Amino-1-(1-naphthyl)-2-methyl-2-propanol was dissolved in 410 mL of isopropanol, and the solution was heated to an inner temperature of 60 to 70° C. A solution of 8.4 g of N-formyl-L-phenylalanine in 410 mL of isopropanol was added to the resulting solution. Then, the mixture was allowed to stand overnight and the precipitated optically active diastereomeric salt of 1-amino-1-(1-naphthyl)-2-methyl-2-propanol and N-formyl-L-phenylalanine was isolated by filtration. The filtered diastereomeric salt was washed with 50 mL of cold isopropanol to obtain a diastereomeric salt. The diastereomeric salt was again mixed with 750 mL of isopropanol and 40 mL of water and the resulting mixture was heated to a reflux temperature to dissolve the diastereomeric salt. Then, the resulting solution was cooled to room temperature and the precipitated diastereomeric salt was isolated by filtration. The filtered diastereomeric salt was washed with 50 mL of cold isopropanol to obtain 14.2 g of a white crystal of the diastereomeric salt.

The melting point of the diastereomeric salt 186 to 188° C. Elementary analysis values: C: 69.8%, H: 7.0%, and N: 6.7% (theoretical value C: 70.6%, H: 6.9%, N: 6.9%).

60 mL of an aqueous 1 mol/L sodium hydroxide solution, 80 mL of water, and 300 mL of chloroform were added to 13.8 g of the diastereomeric salt obtained. Extraction treatment was carried out at room temperature and an organic layer and an aqueous layer were separated. The organic layer obtained was washed with water and concentrated to obtain 5.6 g of (S)-1-amino-1-(1-naphthyl)-2-methyl-2-propanol (yield: 24%). Optical purity: S isomer ratio=99.95%

Analysis results of (S)-1-amino-1-(1-naphthyl)-2-methyl-2-propanol:

[α] D (c 0.5, CH$_3$OH) +60.4°: melting point 86 to 87° C.: $^1$H-NMR (300 MHz, CDCl$_3$, TMS standard) spectrum δ(ppm); 1.07 (3H, s), 1.29 (3H, s), 1.50-2.16 (2H, br), 2.16-3.22 (1H, br), 4.83 (1H, s), 7.46-8.19 (7H, m) Elementary analysis values: C: 77.8%, H: 7.9%, and N: 6.4% (theoretical value C: 78.1%, H: 8.0%, N: 6.5%.

Example 9

24.0 g of 1-Amino-1-(2-naphthyl)-2-methyl-2-propanol was dissolved in 410 mL of isopropanol and the resulting solution was heated to an inner temperature of 40° C. A solution of 8.3 g of N-formyl-L-phenylalanine in 410 mL of isopropanol was added to the resulting solution. Then, the mixture was allowed to stand overnight and the precipitated optically active diastereomeric salt of 1-amino-1-(2-naphthyl)-2-methyl-2-propanol and N-formyl-L-phenylalanine was isolated by filtration. The filtered diastereomeric salt was washed with 50 mL of cold isopropanol to obtain a diastereomeric salt. The diastereomeric salt was again mixed with 750 mL of isopropanol and 40 mL of water and the resulting mixture was heated to a reflux temperature to dissolve the diastereomeric salt. Then, the resulting solution was cooled to room temperature and the precipitated diastereomeric salt was isolated by filtration. The filtered diastereomeric salt was washed with 50 mL of cold isopropanol to obtain 12.4 g of a white crystal of diastereomeric salt.

The melting point of the diastereomeric salt 193 to 195° C. Elementary analysis values: C: 70.4%, H: 6.9%, and N: 6.8% (theoretical value C: 70.6%, H: 6.9%, N: 6.9%).

35 mL of an aqueous 1 mol/L sodium hydroxide solution, 100 mL of water, and 300 mL of chloroform were added to 11.9 g of the diastereomeric salt obtained. Extraction treatment was carried out at room temperature and an organic layer and an aqueous layer were separated. The organic layer obtained was washed with water and concentrated to obtain 6.2 g of (S)-1-amino-1-(2-naphthyl)-2-methyl-2-propanol (yield: 26%). Optical purity: S isomer ratio=99.89%

Analysis results of (S)-1-amino-1-(2-naphthyl)-2-methyl-2-propanol:

[α] D (c 0.5, CH$_3$OH) +14.1°: melting point 77 to 78° C.: $^1$H-NMR (300 MHz, CDCl$_3$, TMS standard) spectrum δ(ppm); 1.09 (3H, s), 1.26 (3H, s), 1.47-2.35 (2H, br), 2.35-3.20 (1H, br), 3.97 (1H, s), 7.44-7.83 (7H, m) Elementary analysis. values: C: 78.0%, H: 8.0%, and N: 6.4% (theoretical value C: 78.1%, H: 8.0%, N: 6.5%.

Example 10

33 mL of thionyl chloride was added dropwise to a mixture of 50.3 g of 1-naphthylglycine (racemic modification) and 200 mL of methanol (dehydrated) at an inner temperature of 35° C. over 1 hour and the mixture was stirred at the same temperature for 3 hours to effect reaction. The reaction mixture was concentrated and the concentrated residue obtained was mixed with 200 mL of diethyl ether. Then, the crystals produced were isolated by filtration and washed with 50 mL of diethyl ether. The crystals isolated by filtration were dried at an inner temperature of 50° C. under reduced pressure to obtain 61.9 g of ochre 1-naphthylglycine methyl ester hydrochloride (yield: 98%).

After 72 mL of triethylamine was added dropwise to a mixture of the 61.9 g of above-obtained 1-naphthylglycine methyl ester hydrochloride and 390 mL of dichloromethane at an inner temperature of −40 to −50° C., 38 mL of trifluoroacetic anhydride was further added dropwise thereto at −45 to −50° C. over 1 hour. The mixture was further stirred at the same temperature for 1 hour to effect reaction and then, the reaction mixture was allowed to warm to 0° C. A mixture of 280 mL of cold water and 10 mL of concentrated hydrochloric acid was added to the reaction mixture and extraction treatment was carried out with 1,100 mL of dichloromethane. The organic layer obtained was washed with 280 mL of cold water. The organic layer obtained was dried over dehydrated sodium sulfate and then concentrated, and the precipitated crystals were filtered. After washing with cold dichloromethane, the crystals were dried at 60° C. inner temperature under reduced pressure to obtain 51.7 g of white N-(trifluoroacetyl)-1-naphthylglycine methyl ester (yield: 68%).

Melting point of N-(trifluoroacetyl)-1-naphthylglycine methyl ester: 183 to 184° C. $^1$H-NMR (300 MHz, CDCl$_3$, TMS standard) spectrum δ(ppm); 3.76 (3H, s), 6.31 (1H, d), 7.30-7.40 (1H, br), 7.46-8.10 (7H, m).

A solution obtained by adding 360 mL of tetrahydrofuran (dehydrated) to a solution of methyl magnesium bromide in 180 mL of tetrahydrofuran (3 moles/L) was cooled to an inner temperature of 0 to 5° C. and at the same temperature, a mixture containing 33.7 g of the above-obtained N-(trifluoroacetyl)-1-naphthylglycine methyl ester and 170 mL of tetrahydrofuran (dehydrated) was added dropwise thereto over 30 minutes. The resulting mixture was allowed to warm to room temperature and stirred at the same temperature for 2.5 hours to effect reaction. The reaction mixture was added to a mixture of 900 g of ice and 200 mL of concentrated hydrochloric acid while maintaining the inner temperature at 5° C. or lower, and extraction treatment was carried out with 800 mL of cold toluene. The aqueous layer obtained was extracted with 800 mL of cold toluene. The organic layer obtained was combined with the previously obtained organic layer and the mixture was washed with 400 mL of cold water. The organic layer obtained was dried over dehydrated sodium sulfate and then concentrated and the concentrated residue was dried at room temperature under reduced pressure to obtain 36.0 g of pale yellow, viscous and oily 1-(trifluoroacetylamino)-1-(1-naphthyl)-2-methyl-2-propanol.

$^1$H-NMR (300 MHz, CDCl$_3$, TMS standard) spectrum of 1-(trifluoroacetylamino)-1-(1-naphthyl)-2-methyl-2-propanol δ(ppm); 0.98 (3H, s), 1.47 (3H, s), 5.83 (1H, d) 7.46-7.89 (7H, m), 8.18 (1H, d).

180 mL of isopropanol and 180 mL of ethanol were added to 36.0 g of the 1-(trifluoroacetylamino)-1-(1-naphthyl)-2-methyl-2-propanol obtained, and 63 g of an aqueous solution of 22% by weight of potassium hydroxide was added-dropwise thereto over 30 minutes at room temperature. The inner temperature of the mixture was raised to 50° C. and, at the same temperature, the mixture was stirred for 2 hours to effect reaction. The reaction mixture was concentrated, and 500 mL of chloroform and 180 mL of water were added to the resulting concentrated residue to carry out extraction treatment. The organic layer obtained was washed with 100 mL of water and the organic layer obtained was dried over dehydrated sodium sulfate and then concentrated. The resulting concentrated residue was dried at an inner temperature of 30° C. under reduced pressure to obtain 28.0 g of brown, viscous and oily 1-amino-1-(1-naphthyl)-2-methyl-2-propanol.

$^1$H-NMR (300 MHz, CDCl$_3$, TMS standard) spectrum of 1-amino-1-(1-naphthyl)-2-methyl-2-propanol δ(ppm); 1.07 (3H, s), 1.29 (3H, s), 1.48-2.94 (3H, br) 4.83 (1H, s) 7.46-8.19 (7H, m).

Example 11

33 mL of thionyl chloride was added dropwise to a mixture of 50.3 g of 2-naphthylglycine (racemic body) and 200 mL of methanol (dehydrated) at an inner temperature of 35° C. inner temperature over 1 hour and the mixture was stirred at the same temperature for 3 hours to effect reaction. The reaction mixture was concentrated and the resulting concentrated residue was mixed with 200 mL of diethyl ether. Then, the crystals produced were recovered by filtration and washed with 50 mL of diethyl ether. The crystals recovered by filtration were dried at an inner temperature of 50° C. under reduced pressure to obtain 59.0 g of white 2-naphthylglycine methyl ester hydrochloride (yield: 94%).

After a mixture of 59.0 g of the above-obtained 2-naphthylglycine methyl ester hydrochloride and 1,180 mL of dichloromethane was cooled, 69 mL of triethylamine was added dropwise to the mixture at an inner temperature of −35 to −38° C. 38 mL of Trifluoroacetic anhydride was further added dropwise thereto at an inner temperature of −40 to −42° C. over 70 minutes. The mixture was further stirred at the same temperature for 1 hour to effect reaction and then, the reaction mixture was allowed to warm to 0° C. A mixture of 280 mL of cold water and 4 mL of concentrated hydrochloric acid was added to the reaction mixture and extraction treatment was carried out with 500 mL of dichloromethane. The organic layer obtained was washed with 280 mL of cold water. The organic layer obtained was dried over dehydrated sodium sulfate and then concentrated and the precipitated crystals were filtered. After washed with cold dichloromethane/n-hexane=1/1 (by volume), the crystals were dried at an inner temperature of 60° C. under reduced pressure to obtain 55.5 g of white N-(trifluoroacetyl)-2-naphthylglycine methyl ester (yield: 76%).

$^1$H-NMR (300 MHz, CDCl$_3$, TMS standard) spectrum of N-(trifluoroacetyl)-2-naphthylglycine methyl ester δ(ppm); 3.77 (3H, s), 5.72 (1H, d), 7.41-7.88 (8H, m).

A solution obtained by adding 390 mL of tetrahydrofuran (dehydrated) to a solution of methylmagnesium bromide in 200 mL of tetrahydrofuran (3 moles/L) was cooled to an inner temperature of 0 to 5° C. and, at the same temperature, a mixture containing 37.0 g of the above obtained N-(trifluoroacetyl)-2-naphthylglycine methyl ester and 190 mL of tetrahydrofuran (dehydrated) was added dropwise over 30 minutes. The resulting mixture was allowed to warm to room temperature and stirred at the same temperature for 2.5 hours to effect reaction. After the reaction mixture was added to a mixture of 900 g of ice and 220 mL of concentrated hydrochloric acid while maintaining the inner temperature at 5° C. or lower, extraction treatment was carried out with 800 mL of cold toluene. The aqueous layer obtained was extracted with 800 mL of cold toluene. The organic layer obtained was combined with the previously obtained organic layer and washed with 400 mL of cold water. The organic layer obtained was dried over dehydrated sodium sulfate and then concentrated. The concentrated residue was dried at an inner temperature of 35° C. under reduced pressure to obtain 36.0 g of a white yellow solid of 1-(trifluoroacetylamino)-1-(2-naphthyl)-2-methyl-2-propanol.

$^1$H-NMR (300 MHz, CDCl$_3$, TMS standard) spectrum of 1-(trifluoroacetylamino)-1-(2-naphthyl)-2-methyl-2-propanol δ(ppm); 1.09 (3H, s), 1.42 (3H, s), 4.95 (1H, d) 7.43-7.85 (8H, m).

After 170 mL of isopropanol and 170 mL of ethanol were added to 36.0 g of the 1-(trifluoroacetylamino)-1-(2-naphthyl)-2-methyl-2-propanol obtained, 56 g of an aqueous solution of 22% by weight of potassium hydroxide was added dropwise thereto over 30 minutes at room temperature. Then, the inner temperature of the mixture was raised to 50° C. and at the same temperature, the mixture was stirred for 2 hours to effect reaction. The reaction mixture was concentrated, and 320 mL of chloroform and 160 mL of water were added to the resulting concentrated residue to carry out extraction treatment. The organic layer obtained was washed with 80 mL of water and the organic layer obtained was dried over dehydrated sodium sulfate and then concentrated. The resulting concentrated residue was dried at an inner temperature of 30° C. under reduced pressure to obtain 24.3 g of a brown solid of 1-amino-1-(2-naphthyl)-2-methyl-2-propanol (yield: 97%).

$^1$H-NMR (300 MHz, CDCl$_3$, TMS standard) spectrum of 1-amino-1-(2-naphthyl)-2-methyl-2-propanol δ(ppm); 1.08 (3H, s), 1.26 (3H, s), 1.46-3.05 (3H, br) 3.96 (1H, s) 7.42-7.84 (7H, m).

The invention claimed is:

1. A process for producing an optically active cyclopropane compound represented by the formula (7):

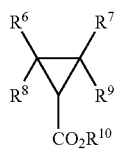

(7)

wherein $R^6$, $R^7$, $R^8$, and $R^9$ are the same or different, and independently represent a hydrogen atom, an alkyl group optionally substituted with a halogen atom, an alkenyl group optionally substituted with a halogen atom, a substituted or unsubstituted aryl or aralkyl group; provided that, when $R^6$ and $R^8$ are the same, $R^6$ and $R^7$ are different from each other; and $R^{10}$ represents a C$_{1-6}$ alkyl group, which comprises reacting a prochiral olefin represented by the formula (5):

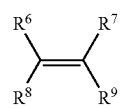

(5)

wherein $R^6$, $R^7$, $R^8$, and $R^9$ are as described above, with a diazoacetic acid ester represented by the formula (6):

N$_2$CHCO$_2$R$^{10}$ (6)

wherein $R^{10}$ is as defined above: in the presence of the asymmetric copper complex, which is (I) an asymmetric copper complex produced from a copper compound and the optically active bisoxazoline compound represented by the formula (1):

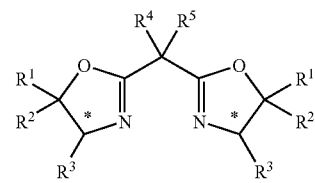

(1)

wherein $R^1$ and $R^2$ are the same, and each represents a C$_{1-6}$ alkyl group; $R^3$ represents a 1-naphthyl group or a 2-naphthyl group; $R^4$ and $R^5$ are the same and each represents a hydrogen atom or a C$_{1-3}$ alkyl group, or $R^4$ and $R^5$ are bonded each other together with the carbon atom to which they are bonded to form a cycloalkyl ring having 3 to 6 carbon atoms; and * represents an asymmetric center, or (II) an asymmetric copper complex produced from a copper compound and the optically active bisoxazoline compound represented by the formula (1):

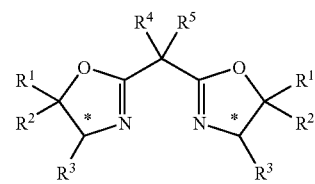

(1)

wherein $R^1$ and $R^2$ are the same, and each represents a C$_{1-6}$ alkyl group; $R^3$ represents a 1-naphthyl group or a 2-naphthyl group; $R^4$ and $R^5$ are the same and each represents a hydrogen atom or a C$_{1-3}$ alkyl group, or $R^4$ and $R^5$ are bonded each other together with the carbon atom to which they are bonded to form a cycloalkyl ring having 3 to 6 carbon atoms; and * represents an asymmetric center, wherein the configurations of two asymmetric carbon atoms represented by * are both (S), or (R).

* * * * *